(12) United States Patent
Garver et al.

(10) Patent No.: US 6,474,354 B2
(45) Date of Patent: *Nov. 5, 2002

(54) ON-LINE SENSOR FOR COLLOIDAL SUBSTANCES

(75) Inventors: Theodore M. Garver, Edmonton (CA); Kenneth Boegh, Thunder Bay (CA); Yuan Hongqi, Edmonton (CA)

(73) Assignee: Alberta Research Council Inc., Alberta (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/877,203

(22) Filed: Jun. 11, 2001

(65) Prior Publication Data

US 2002/0011266 A1 Jan. 31, 2002

Related U.S. Application Data

(63) Continuation-in-part of application No. 09/422,269, filed on Sep. 18, 1998, now Pat. No. 6,263,725.

(30) Foreign Application Priority Data

Sep. 18, 1997 (CA) .............................................. 2216046

(51) Int. Cl.⁷ .............................................. G05D 11/13
(52) U.S. Cl. .......................... 137/2; 73/61.48; 73/61.71; 137/93
(58) Field of Search ...................... 137/2, 93; 73/61.71, 73/61.48

(56) References Cited

U.S. PATENT DOCUMENTS

| | | | |
|---|---|---|---|
| 4,318,180 A | 3/1982 | Lundqvist et al. | |
| 4,752,131 A | 6/1988 | Eisenlauer et al. | |
| 4,791,305 A | 12/1988 | Karaila | |
| 4,964,955 A | 10/1990 | Lamar et al. | |
| 4,999,514 A | 3/1991 | Silveston | |
| 5,266,166 A | 11/1993 | Dreisbach | |
| 5,331,177 A | 7/1994 | Kubiasak et al. | |
| 5,453,832 A | 9/1995 | Joyce | |
| 5,468,396 A | 11/1995 | Allen et al. | |
| 5,576,827 A | 11/1996 | Strickland et al. | |
| 5,676,796 A | 10/1997 | Cutts | |
| 6,072,309 A | * 6/2000 | Watson et al. | 324/452 |
| 6,134,952 A | * 10/2000 | Garver et al. | 162/49 |
| 6,263,725 B1 | * 7/2001 | Garver et al. | 250/372 |

OTHER PUBLICATIONS

Evans et al., "The Colloidal Domain: Where Physics, Chemistry, Biology and Technology Meet", 1994, pp. 325–362, VCH Publishers, New York.

* cited by examiner

Primary Examiner—Stephen M. Hepperle
(74) Attorney, Agent, or Firm—Freedman & Associates

(57) ABSTRACT

A method and apparatus for determining and controlling a property of colloidal substances that undergo at least one of a temperature dependent phase transition and a temperature dependent adsorption-desorption process is disclosed. The colloidal particles are characterized by performing successive measurements of light attenuation or emission by a colloidal mixture at two or more temperatures and at one or more wavelength. The difference or ratio of the measurements at two or more temperatures provides a measure of the colloidal stability with respect to temperature. The amount of certain organic colloids that are unstable to temperature variation may be determined from the magnitude of the measurement change. This method may be specifically applied to determining the tackiness and propensity to deposit of colloidal pitch or wood resin in pulp or paper process water as an indication of the effectiveness of a chemical control program. In this context a feedback signal may be provided for use by a process controller to achieve improved process control.

38 Claims, 27 Drawing Sheets

ON-LINE SENSOR FOR COLLOIDAL SUBSTANCES

This application is a continuation-in-part of U.S. patent application Ser. No. 09/422,269 filed Sep. 18, 1998, now U.S. Pat. No. 6,263,725.

FIELD OF THE INVENTION

This invention relates generally to the application of ultraviolet-visible light measurements for the determination of colloidal substances in a liquid sample. More particularly, the invention relates to the application of light attenuance and/or light scattering measurements for determining and controlling a property of colloidal substances that undergo at least one of a temperature dependent phase transition and a temperature dependent adsorption-desorption process.

BACKGROUND OF THE INVENTION

Papermaker's demands for high speed and efficiency, flexible manufacturing, stringent quality standards, and environmental compatibility coupled with new developments in on-line process control are driving the development of new sensor technology for the paper machine wet-end. The need for better systems for providing wet-end chemistry control is emphasized by recent reports stating that only 10% of the world's 150 newsprint paper machines operate at an efficiency above 88%, and that more than 60% operate in the low efficiency range below 82.5%, see for example Mardon, J., Chinn, G. P., O'Blenes, G., Robertson, G., Tkacz, A. Pulp and Paper Canada, Vol. 99 No. 5 pp. 43–46. (1998). William E. Scott addressed some of the problems that are related to wet-end chemistry control in *Principles of Wet End Chemistry*. Tappi Press, Atlanta, 1996. p. 3. "Deposits and scale usually arise from out-of-control wet end chemistry. Typical examples include chemical additive overdosing, charge imbalances, chemical incompatibility and the shifting of chemical equilibria. All of these phenomena can lead to the formation of precipitates or colloidal aggregates that produce deposits and scale. While there are numerous approaches to treating the symptoms of deposits the best approach is to determine what is out of control and fix it."

Pitch is a generic term for the colloidal components that are suspended in the pulping process waters or water of the paper machine wet-end, wherein the composition of individual pitch particles may vary from relatively pure mixtures of fresh resin and fatty acids to heterogeneous agglomerations of wood extractives, wood-derived lignin and hemicellulose, salt, cationic polymer and filler particle. The common use of the term pitch often blurs the distinction between extractives, pitch, white pitch, and stickies as defined in the Dictionary of Paper $5^{th}$ Edition, Tappi Press, 1996, Atlanta Ga. The degree to which temperature will alter the equilibria between colloidal pitch and dissolved substances is a complicated function of the solution conditions and the composition of the pitch particle itself. In the field of pulp and paper manufacture the maintenance of a level of stability and/or the removal of colloidal pitch is an important objective in the wet-end chemistry control programs. Deposition leading to poor paper machine efficiency is a costly problem, which is addressed through numerous strategies including pulp processing optimization and/or addition of chemical agents.

Nearly every pulp and paper mill has a strategy for controlling pitch to prevent its deposition on pulping, bleaching and papermaking machinery and to reduce pitch build-up in white water systems. Pitch control strategies include: stabilization with dispersants; coagulation and fixation with cationic polymers; and, adsorption and removal with mineral additives such as talc or bentonite clay, as described by Garver Jr., T. M. and Yuan, H. *Measuring the response of pitch control strategies.* in *PAPTAC 87th Annual Meeting.* 2001. Montreal, the contents of which are incorporated by reference herein. A strategy utilizing dispersants, such as for example non-ionic surfactants, is usually employed in open systems where the dispersed colloids can go to drain, while a strategy of removal with cationic polymers or talc is typically used in closed systems where the incoming pitch must be removed with the product. In addition, there is a plurality of pulp processing variables that may be adjusted in an attempt to reduce pitch accumulation and deposition. Ultimately the single most important reason for controlling pitch is the cost of lost production time related to cleaning pitch deposition on equipment. Other factors related to product quality include such issues as increased dirt and speck counts from agglomerated pitch or sloughed off deposits and loss of paper strength related to the interference of resinous substances with interfiber bonding and surface tension that is important for wet strength.

A method for controlling pitch using micro-particle bentonite addition with cationic polymer flocculation is disclosed in U.S. Pat. No. 5,676,796, issued to Cutts on Oct. 14, 1997. Another combination using kaolin as inorganic colloid and poly(diallyldimethyl-ammonium chloride) cationic polymer is disclosed by Lamar; Pratt; Weber and Roeder in U.S. Pat. No. 4,964,955, which issued Oct. 23, 1990. Alternatively, Dreisbach and Barton disclose a method of preventing pitch deposits by the addition of a nonionic polymeric dispersing agent in U.S. Pat. No. 5,266,166, issued Nov. 30, 1993. A physical process for reducing wood resin pitch from wood process water employing a centrifuge is disclosed by Allen and Lapointe in U.S. Pat. No. 5,468, 396, issued Nov. 21, 1995. Of course, any method for controlling pitch by the addition of chemical agents requires rapid analysis of the process water to avoid accidental overdosing or underdosing of the chemical agents, which would produce undesirable results or which would increase unnecessarily the overall cost of the process control program.

A plurality of instruments for relating the intensity and/or angular dependence of scattered or absorbed light to the total concentration or size distribution of colloids are known in the prior art. For example, instruments for characterizing the amount of colloidal particles on the basis of light scattering measurements (nepholometry) and light attenuation measurements (turbidimetry) are commercially available as laboratory, hand-held and on-line instruments. On-line turbidimeters measure the intensity of light that is detected in-line and at an angle to a source of incident light. The turbidimeter relates a ratio of the detected intensities of light to a turbidity value in Jackson or NTU units. U.S. Pat. No. 4,999,514, issued Mar. 12, 1991 in the name of Silveston, discloses a method for controlling the intensity of the light source to provide a turbidimeter that operates over a broad range of particle concentrations. Kubisiak and Wilson in U.S. Pat. No. 5,331,177 describe an analog to digital turbitimeter apparatus that provides a measure of the change in turbidity over time. Other, more sophisticated methods, involving the analysis of the time and spatial dependence of light attenuation and scattering may provide information on particle size distributions, as taught by Strickland et al. in U.S. Pat. No. 5,576,827 and the patents referenced therein. Instrumentation specifically designed for measuring particle and fiber size distributions in low consistency (<1%) pulp suspensions by analysis of the time and spatial variation of scattered or absorbed light includes the BTG-Spectris RET-5300 or the Metso Automation RM200 Retention Monitoring System. These instruments employ methods taught by Lundqvist; Pettersson and Fladda in U.S. Pat. No. 4,318,180.

Unfortunately, the prior art instruments are other than capable of differentiating colloidal wood-derived pitch particles from similarly sized colloidal clay particles and hence the measured concentration represents the total concentration of all colloidal species in suspension. As such, methods to measure the amount of a specific colloidal component in a mixture or to rapidly evaluate the temperature stability of a colloidal suspension are not readily available. Additionally, systems for obtaining on-line measurements of colloid tackiness or the propensity for a colloid to agglomerate or to deposit onto a surface currently are not available. Further additionally, no measurement systems exist currently that provides a measure of the capacity of a colloid to adsorb and/or desorb other dissolved or colloidal substances.

Ideally, on-line measurements would assist with selection and/or design, optimization and control of chemical programs to reduce pitch deposition. These measurements would evaluate deposition rate and propensity toward deposition as the most relevant feedback indicator for the control of pitch management programs. In general, the currently available methods for evaluating pitch concentration, deposition, deposition tendency and tackiness are time consuming and provide insufficient reproducibility and insufficient information to be generally useful for the control of pitch in paper mills. Methods to evaluate and systematically improve pitch control chemical formulations and on-line methods for quantifying pitch are practically nonexistent. Laboratory methods, however, are known and include quantification of pitch concentration by colloidal pitch counts using microscopy or a laser particle counter. Allen in Trans. Tech Sect disclosed the accepted laboratory method of pitch analysis using microscopy. CPPA 3(2):32 (1977). This procedure is time consuming, as it has not yet been successfully automated by computerized image analysis techniques. An instrumental method employing a laser beam to count particles flowing through a capillary has been described by Eisenlauer; Horn; Ditter; Eipel in U.S. Pat. No. 4,752,131. The laser method, known as a pitch counter, requires expensive and specialized instrumentation that is not easily adapted to analysis in an industrial setting.

The turbidity of a suspension is also widely used as a measure of the concentration of suspended pitch particles, and there is some hope of achieving on-line turbidity measurements of colloids removed from a fiber suspension. Turbidity measures a concentration of colloids, however, the propensity for colloids to deposit is governed not only by the concentration but also by the forces between surfaces and the colloid particles. To the best of our knowledge, a variable temperature turbiditimeter currently is not commercially available.

Several technically simple tests for gravimetrically measuring deposition have also been described in the prior art. Other more sophisticated techniques, such as atomic force spectroscopy and jet impingment, may be used to measure deposition or intersurface forces, but methods to directly measure and characterize deposition or pitch tackiness are time consuming and inappropriate for use in mill evaluation. It is for this reason that the factors influencing deposition, such as for example concentration and electrostatic forces, are typically measured. The best available laboratory or on-line instrumentation for characterizing the interaction energies between two particles or between a particle and a surface are instruments for measuring the electrostatic potential at the surface of colloid particles. Zeta or streaming potential or charge measurements are different ways to characterize electrostatic charge and they may be used to monitor and control chemical and physical methods for controlling pitch. Although the surface or total charges are important measures of the colloidal stability, these measurements do not distinguish colloidal pitch from other, less problematic colloids such as added clay. In addition, the measurement of the electrostatic forces for suppression of deposition by a pitch control agent ignores the importance of competing attractive London dispersion forces. Although some efforts have been made to control pitch in dependence upon on-line and off-line turbidity or charge measurements, typically chemical methods for controlling pitch are performed absent real-time feed back control. Despite the high cost of chemical treatment programs and the potential downtime caused by overdosing or underdosing, chemical methods for controlling pitch are often invariant over time, and substantial swings in wet-end chemistry may result.

In view of the need for better instrumentation for pitch characterization, it would be advantageous to provide an instrumental method that characterizes pitch concentration, composition and stability by analysis and interpretation of the wavelength dependence of light attenuation by mixtures of pitch particles. This method may be used to evaluate the effectiveness of chemical treatments for pitch control. The method and the apparatus in accordance with the invention provides for on-line measurements of colloidal substances in a liquid sample. This invention is particularly useful for determining or estimating the amount of colloidal substances in pulp or paper mill process water or effluents. The method and the apparatus in accordance with the invention are able to empirically identify and measure a property related to the size, composition, and concentration of a colloidal mixture. The measurements thus obtained according to the instant invention provide a means to empirically identify and measure a property related to the particle size, composition, and concentration of a colloidal mixture.

OBJECT OF THE INVENTION

It is an object of the instant invention to provide a method and apparatus for rapidly evaluating the response of a characteristic of a colloidal mixture to an addition of an additive thereto.

It is a further object of the instant invention to provide a method and apparatus for providing a feedback signal to a process controller in dependence upon a measured characteristic of the process.

It is an object of the instant invention to provide a method of measuring the propensity of colloids to deposit, to adsorb substances from solution or to aggregate.

SUMMARY OF THE INVENTION

In accordance with an aspect of the invention there is provided a method for controlling a characteristic of a colloidal mixture comprising the steps of:
providing a colloidal mixture for analysis by thermal difference spectroscopy; determining a value indicative of the characteristic of the colloidal mixture by the steps of:
irradiating at least a first portion of the colloidal mixture with light in an ultraviolet-visible region at a first temperature and obtaining a first measurement of a first wavelength within the ultraviolet-visible region, said first measurement for obtaining a measure of one of an absorption, emission and scattering of the first wavelength when said colloidal mixture is irradiated with the light, waiting for the temperature of the colloidal mixture to change, irradiating at least a second portion of the colloidal mixture with light in an ultraviolet-visible region at a second different temperature and obtaining a second measurement of the first wavelength within the ultraviolet-visible region, said second measurement for obtaining a measure of one of an absorption, emission and scattering of the first wavelength when said colloidal mixture is irradiated with the light, and determining the value indicative of the characteristic of the colloidal mixture from a relationship including the first measurement and the second measurement;

determining, in dependence upon the determined value, an adjustment to at least a variable of a control process for affecting at least a characteristic of the colloidal mixture;

providing a feedback signal in dependence upon the determined adjustment to an automated controller of the control process; and adjusting automatically the variable of the control process in dependence upon the provided feedback signal.

In accordance with the aspect of the invention there is further provided a method for controlling a process parameter of a process involving a colloidal mixture comprising the steps of:

providing at least a first portion of the colloidal mixture for an optical measurement by the steps of:

providing a portion of the colloidal mixture to an in-line centrifuge unit to separate particulate matter therefrom, to obtain an approximately fiber-free sample, and providing the approximately fiber-free sample as the at least a first portion;

determining a value indicative of a characteristic of the colloidal mixture by the steps of:

irradiating the at least a first portion of the colloidal mixture with light in an ultraviolet-visible region at a first temperature and obtaining a first measurement of a first wavelength within the ultraviolet-visible region, said first measurement for obtaining a measure of one of an absorption, emission and scattering of the first wavelength when said colloidal mixture is irradiated with the light, and determining the value indicative of the characteristic of the colloidal mixture from a relationship including the first measurement;

determining, in dependence upon the determined value, an adjustment to the process parameter of the process involving the colloidal mixture;

providing to an automated controller of the process involving the colloidal mixture a feedback signal in dependence upon the determined adjustment; and adjusting automatically the process parameter of the process in dependence upon the provided feedback signal.

In accordance with the aspect of the present invention there is still further provided a method for controlling a characteristic of a colloidal mixture comprising the steps of:

providing a colloidal mixture for analysis by thermal difference spectroscopy; determining a value indicative of the characteristic of the colloidal mixture by the steps of:

irradiating at least a first portion of the colloidal mixture with light in an ultraviolet-visible region at a first temperature and obtaining at least a first measurement of a first and a second wavelength within the ultraviolet-visible region, said first measurement for obtaining one of an absorption, emission and scattering of the first wavelength when said colloidal mixture is irradiated with the light, waiting for the temperature of the colloidal mixture to change, irradiating at least a second portion of the colloidal mixture with light in an ultraviolet-visible region at a second different temperature and obtaining at least a second measurement of the first and the second wavelength within the ultraviolet-visible region, said second measurement for obtaining one of an absorption, emission and scattering of the second wavelength when said colloidal mixture is irradiated with the light, and determining the value indicative of the characteristic of the colloidal mixture from a relationship including a ratio of the at least first and second measurement;

determining, in dependence upon the determined value, an adjustment to at least a variable of a control process for affecting at least a characteristic of the colloidal mixture;

providing a feedback signal in dependence upon the determined adjustment to an automated controller of the control process; and adjusting automatically the variable of the control process in dependence upon the provided feedback signal.

In accordance with a second aspect of the invention there is provided an on-line optical sensor apparatus for controlling a process parameter of a process involving a colloidal mixture comprising:

an in-line centrifuge unit for separating fiber from the colloidal mixture to obtain an approximately fiber-free liquid sample;

a detector for obtaining a first measurement and a second measurement of light in an ultraviolet-visible region, said first measurement for obtaining a measure of one of an absorption, emission and scattering of at least a first wavelength of the light at a first temperature when the approximately fiber-free liquid sample of the colloidal mixture is irradiated with the light, and said second measurement for obtaining a measure of one of an absorption, emission and scattering of the first wavelength of the light at a second different temperature when the approximately fiber-free liquid sample of the colloidal mixture is irradiated with the light; and a suitably programmed processor in electrical communication with an automated process controller for providing thereto a signal indicative of an adjustment to the process parameter, wherein said adjustment is determined in dependence upon a characteristic of the colloidal mixture, and wherein said characteristic of the colloidal mixture is determined from a relationship including the first and second measurement.

BRIEF DESCRIPTION OF THE DRAWINGS

Exemplary embodiments of the invention will now be described in accordance with the drawings in which.

DETAILED DESCRIPTION OF THE INVENTION

Figure 1:
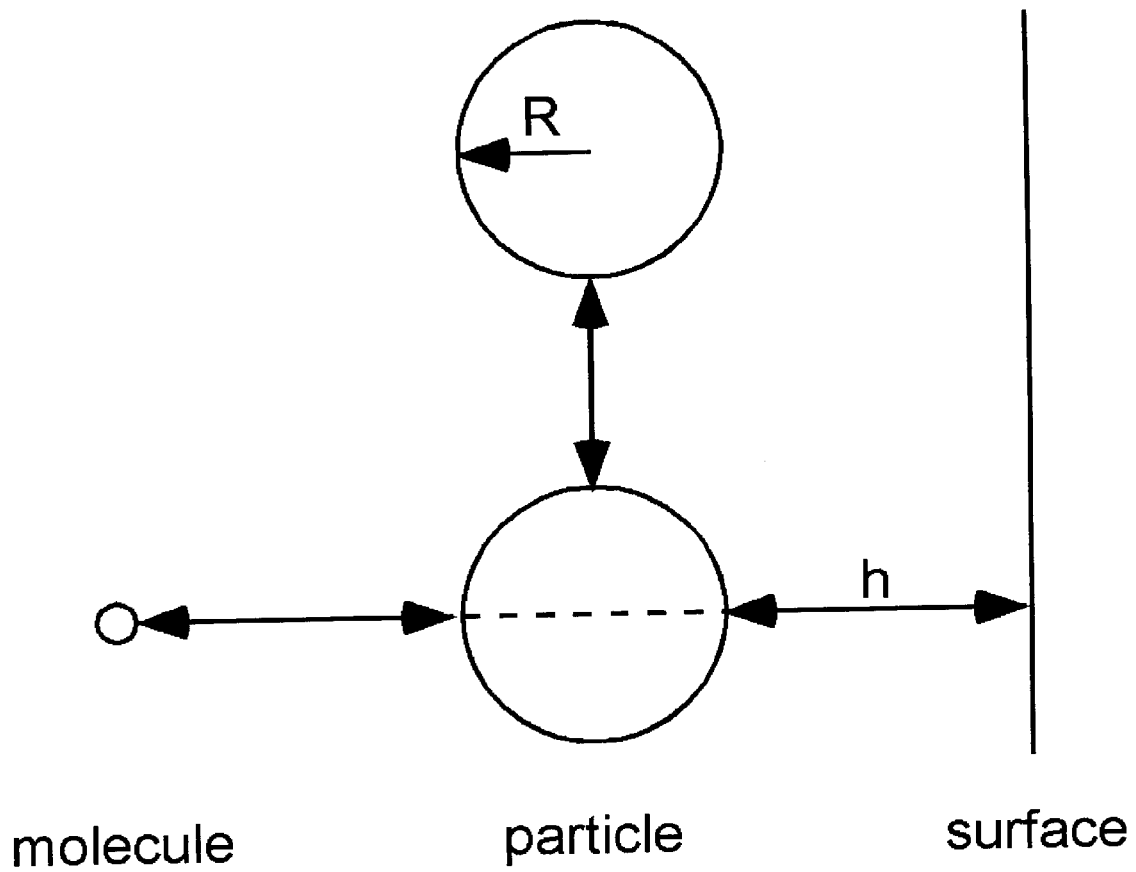
FIG. 1 shows schematically the three types of interactions that are experienced by a colloid particle in a colloidal pitch suspension.

The object of the instant invention requires the use of the variation of an optical property of a liquid sample, due to a temperature-sensitive phase transition of a colloidal substance suspended therein, to determine a quantity of said substance that is susceptible to the phase transition. By way of a specific example, the invention is described in the present disclosure for the analysis of pulp and paper mill process water having temperature sensitive colloidal wood pitch suspended therein. It should be recognized that pitch is a generic term and that the composition of individual pitch particles typically varies from relatively pure mixtures of fresh resin and fatty acids to heterogeneous agglomerations of wood extractives, wood-derived lignin and hemicellulose, salt, cationic polymer and filler particle. The degree to which temperature will alter the equilibria between colloidal pitch and dissolved substances is a complicated function of the solution conditions and of the composition of the pitch particle itself. For example, our laboratory tests have shown that the change in light attenuance measured as a function of temperature is different for a same colloidal mixture that is buffered at different pH values. Further, it has been reported that hemicellulose components may stabilize wood colloidal resin (Sundberg, K; Thornton, J.; Holmbom, B.; and Ekman, R. *Journal of Pulp and Paper Science Vol. 22 Number 7*, 1996, pp J226–J230. We have found, however, that the variations of pH and ionic strength that are typical of a pulp processing or paper making process do not lead to substantial variations of the change in light attenuance measured as a function of temperature for a colloidal mixture. It is expected that variation in the concentrations of components that may lead to coagulation and agglomeration may produce pitch particles that are less sensitive to changes in temperature. The measurement of the temperature dependence of the light attenuation is related specifically to the pitch components that are sensitive to temperature change.

Our analysis is based upon measurement of the wavelength and temperature dependence of the light attenuation (D) when light is passed through a colloidal mixture. Polychromatic light passed through a colloid sample and detected at an array of wavelengths is a complicated function of the light absorption of the liquid, the light absorption of the particles, the light emission by fluorescence from dissolved or colloidal components and the scattering that may deflect light away from or towards the detector. The scattering of particles in the range of 0.1–10 times the wavelength of light (Mie scattering) is a complicated function of wavelength, particle size, concentration, and refractive index of the particles and of the medium. Hence when the attenuation light by the colloidal particles is examined we are actually looking at the light attenuation derived from both scattering and the UV absorbance of the particles. Absorbance corresponds to the light energy that is transformed into another type of energy (typically exciting electrons to higher energy levels, but including exciting vibrations or other sub-molecular events). The wavelength dependence of light attenuation by particles will be a function of the color of the particles, and also the size of the particles. Mie-scattering theory may be solved to back out the particle size distribution from the wavelength dependence of absorption or scattering for a pure or well-characterized substance. But the theory and the calculations are complex and they are certainly cannot be directly applied to analyzing heterogeneous industrial or pulp and paper colloids. The measurements described herein provide a means to empirically identify and measure a property related to the stability, particle size, composition, and concentration of a colloidal mixture. Throughout the present disclosure, and in the claims that follow, we have used the terms absorbance, attenuance and scattering, as defined in *Glossary of Terms Used in Photochemistry* Verhoeven, J. W. Pure & Appl. Chem. 1996, 68, 2223.

The forces that govern the agglomeration of pitch particles or the deposition of pitch particles on equipment surfaces in a paper mill are similar to the forces that exist between a molecule and a particle and between a particle and a surface. Ultimately, we are interested in evaluating pitch tackiness or the propensity of a pitch particle to deposit on a surface. Factors, such as for instance pitch particle concentration and the available surface area, also contribute to the propensity to deposition. The forces between molecules may be grouped into electrostatic forces that are generally repulsive and repulsive and London dispersion forces that are generally attractive. The DLVO theory relates the interaction potential between two particles as shown in equation (1) below, as disclosed in Evans, D. F. and Wennerstrom, H. *The colloidal domain: where physics, chemistry, biology and technology* meet, ed. E. G. Cohen, 1994, New York: VCH Publishers, 325–362.

$$V(h) = \pi R \left\{ -\frac{H_{121}}{12\pi} \frac{1}{h} + \frac{64kTc_0^* \Gamma_0^2}{\kappa^2} \exp(-\kappa h) \right\} \quad (1)$$

The London dispersion forces, which contribute to the attractive terms, are strongly influenced by the Hamaker constant $H_{121}$ which governs the attractive interactions. The repulsive terms are electrostatic and are dependent upon the Debye screening length $\kappa$, which is a function of ionic strength, and the surface potential (buried in the $\Gamma$ constant). FIG. 1 illustrates schematically the three types of interactions: the particle—particle interaction, the particle-surface interaction, and the particle-molecule interaction. The interparticle distance (h), and particle radius (R) influence the strength of each type of interaction.

Figure 2:
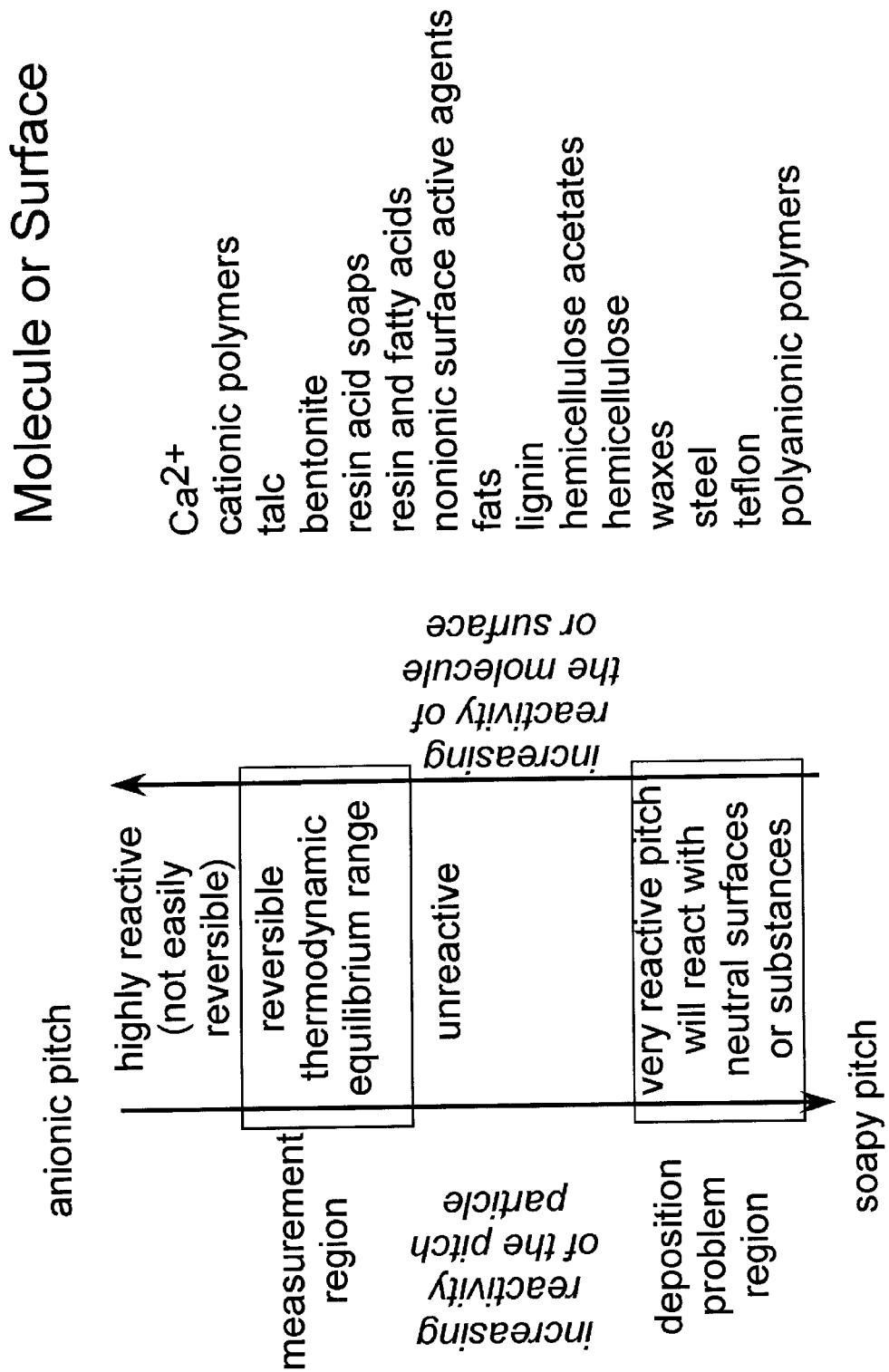
FIG. 2 shows a measurement region.

The changes in light attenuation due to changes in absorbance of dissolved molecules and scattering of colloids provide the experimental basis to monitor the equilibrium between dissolved and colloidal substances. These experiments provide information on to the interaction between a molecule and a colloid particle that is used as a limiting case describing the forces and energy involved in the interaction between two pitch particles or between a particle and a surface. Interactions that may be substantially irreversible on the macroscopic scale of particles interacting with surfaces are smaller and thermodynamically determined for the case of a molecular interaction with the surface. It is in monitoring the magnitude and specificity of the molecular interaction that we may make the connection to the surface reactivity or particle tackiness. The energy limits of a reaction or change of state that is reversed at temperatures between 20 and 80 C is our measurement region as shown in FIG. 2. The measurement region, illustrated in FIG. 2, can "slide" along the continuum between highly reactive pitch to unreactive pitch but in different regions we will be probing the equilibrium with molecules of varying reactivity. The temperature measurement range corresponds to the interaction energy between the surface of a colloid particle and the molecules that reversibly associate with or dissociate from the colloid. The time frame of the measurement determines the kinetic limits to this predominately thermodynamic determined measurement. Using the pitch analyzer, preferably we measure interactions that are weak so that they are essentially reversible.

Figure 3:
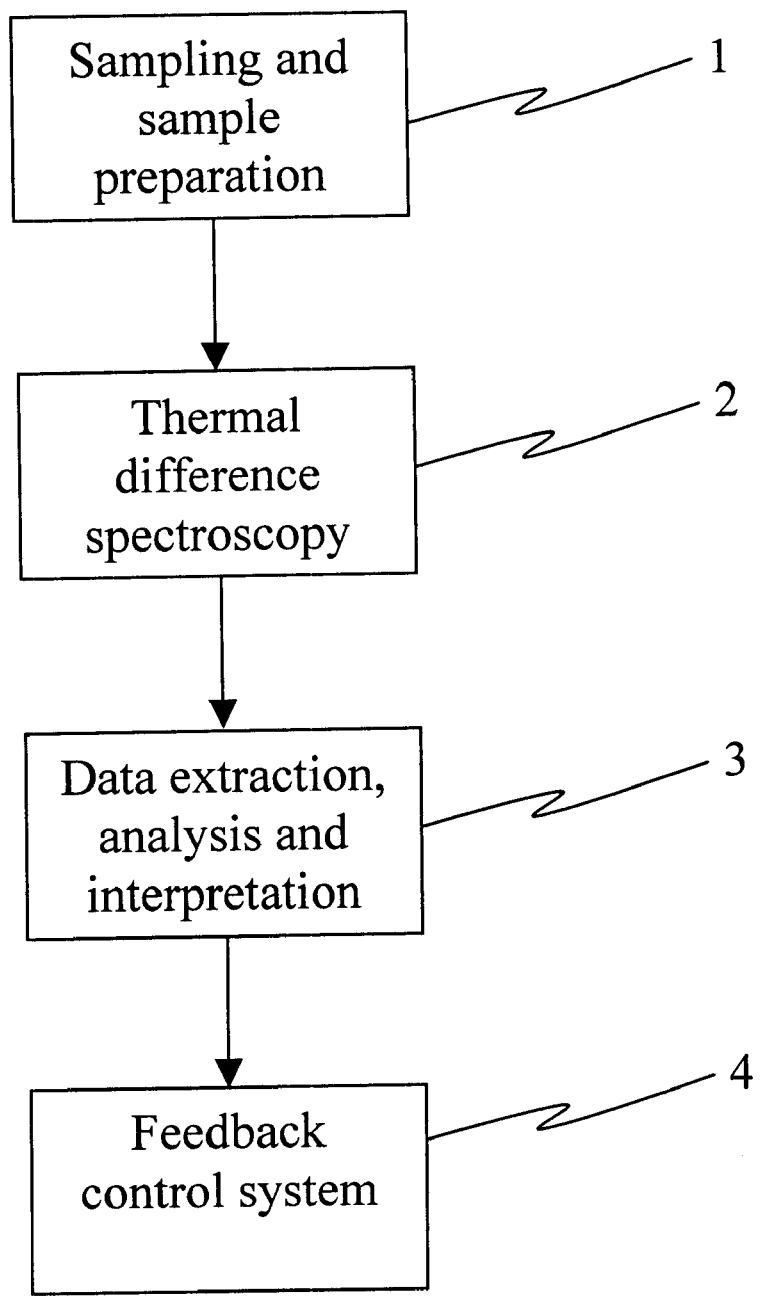
FIG. 3 shows a simplified flow diagram of a system according to the present invention for optically measuring a property of a colloidal suspension and for providing a feed back signal to a process control system in dependence upon said measured property.

Referring now to FIG. 3, shown is a simplified flow diagram of a system in accordance with the present invention for optically measuring a property of a colloidal suspension and for providing a signal in dependence upon said measured property. The system includes a sampling portion 1 in operative communication with an analyzer portion 2. The sampling portion 1 is for obtaining a sample of process water having colloidal matter suspended therein, such as for example colloidal wood pitch, and for providing a fiber-free colloidal sample to the analyzer portion 2. The sampling portion 1 and the analyzer portion 2 are also in electrical communication with a controller portion 3 having a microprocessor for executing program code thereon (microprocessor not shown). In use, the analyzer portion 2 optically measures a property of the fiber-free colloidal sample and provides light attenuance data to the controller unit 3 for at least one of extraction, analysis and interpretation of the data. The controller portion 3 is also in electrical communication with a feedback control portion 4 such that, in use, the controller portion 3 provides a signal to the feedback control portion 4 in dependence upon the measured property, the signal being indicative of a process variable adjustment for affecting one of the measured property and another property of the process water.

Figure 4:
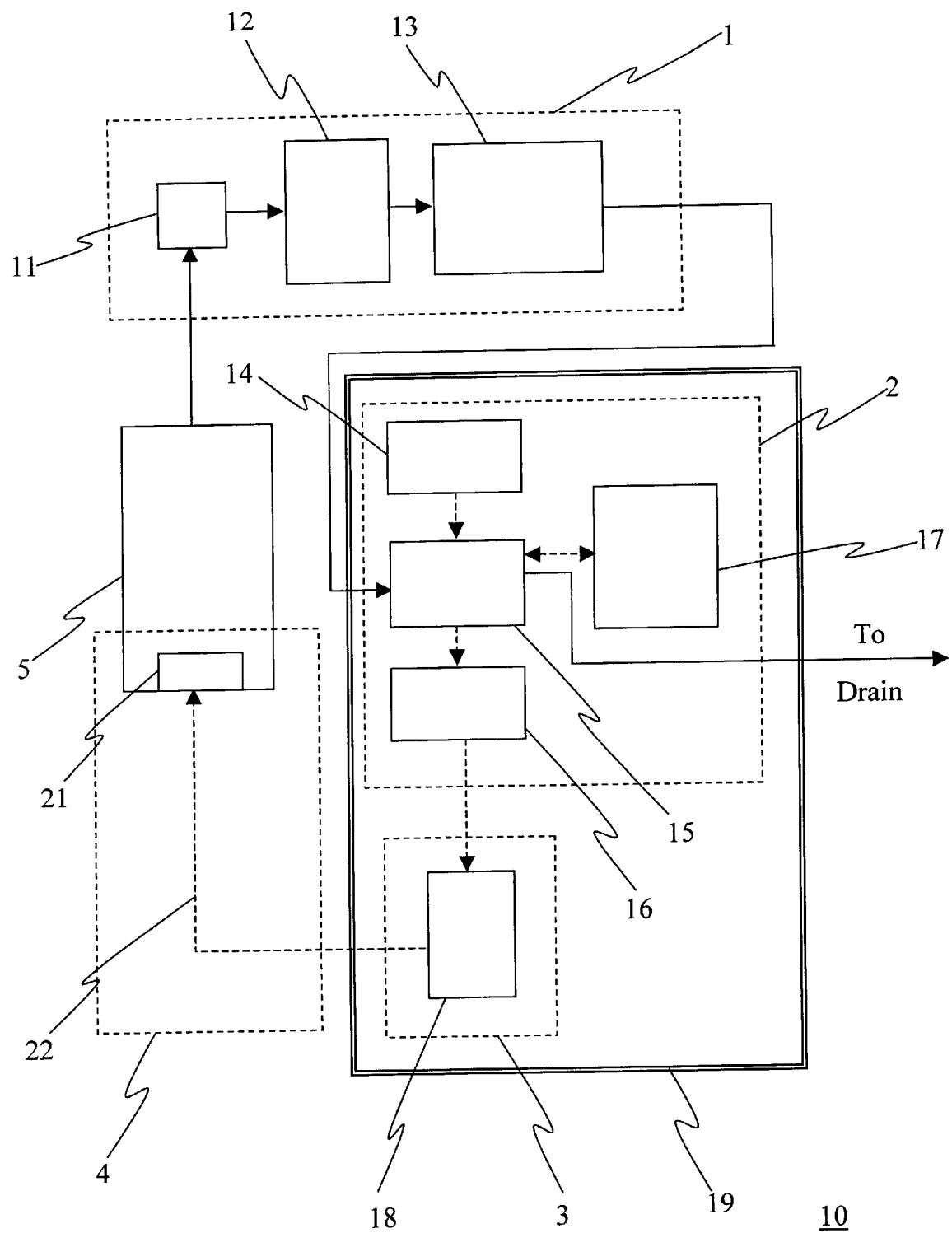
FIG. 4 shows a simplified block diagram of a system according to the present invention for optically measuring a property of a colloidal suspension and for providing a feed back signal to a process control system in dependence upon said measured property.

Referring now to FIG. 4, shown is a simplified block diagram of an on-line sensor system 10 for the analysis of colloidal mixtures in accordance with the present invention. Process water is sampled from a process 5 by a sample manifold 11. The sample manifold provides the process water to a separation unit 12, which removes suspended wood fiber and provides a fiber-free sample to a sample manager and cleaning unit (SMCU) 13. In FIG. 4 the dashed lines indicate data communication paths and the solid lines indicate sample tubing for transferring process water throughout system 10. The system 10 is controlled by the controller portion 3 which includes at least a processor 18. The processor 18 controls the operations of the sampling portion 1, the analyzer portion 2 and the feedback control portion 4. The electrical connections between said portions are well known in the art and have been omitted from FIG. 4 for the sake of clarity.

The processor 18 is in electrical communication with the sample manifold 11 for controlling the operation of a valve or of a plurality of valves (not shown) of the sample manifold 11. In a preferred embodiment, six ball valves are actuated in sequence by the processor 18. The sample manifold 11 allows a plurality of water or pulp slurry samples to be sampled on-line from the process 5. The liquid sample is then delivered from the sample manifold 11 to the separation unit 12. The separation unit 12 provides a fiber-free liquid sample to the SMCU 13 and returns the remaining sample back into the process 5. In a preferred embodiment the separation unit 12 is a centrifuge-based separation unit 12a, the operation of which is controlled by the processor 18 and is explained in detail below with reference to FIG. 5. Alternatively, the separation unit 12 is a filter-based separation unit 12b, the operation of which is also controlled by the processor 18 and is explained in more detail below, see FIG. 6. Of course, the usefulness of the present invention is extended by extraction of liquid samples from high consistency pulp slurry before final removal of the fiber in the separation unit 12.

The operation of the SMCU 13 is controlled by the processor 18. In one mode of operation the SMCU 13 delivers the liquid sample to a temperature controlled dual UV cell holder (DUVCH) 15 for obtaining a UV measurement and in another mode of operation it delivers a cleaning fluid to the temperature controlled DUVCH 15 for cleaning said DUVCH. Both, the liquid sample and the cleaning fluid are delivered to the DUVCH 15 by means of a pump (not shown), such as a Cole Palmer variable speed peristaltic pump P-77962-10.

In a preferred embodiment, the DUVCH 15 has a temperature controlled, stirred, flow-through cell with a pathlength that is typically 1 mm integrated into a temperature control unit with a Peltier Effect thermoelectric heat pump. This system is optimized for thermal transfer to the system using thermally conductive materials with Peltier thermoelectric heat pumps in close proximity to the observed sample. The DUVCH 15 allows for UV measurements to be taken at a plurality of temperatures. Alternately, the DUVCH 15 has 2 UV cells, one 1.0 mm flow-through quartz UV cell (UV region, short wavelength) and another 10.0 mm flow-through quartz UV cell (visible region, long wavelength). This is desired since the attenuance in the visible region is very low and requires a cell having a longer path length and vice versa, the attenuance in the UV region is very intense and a cell having a shorter path length is more desirable. The processor 18 controls the operation of a temperature controller 17, for instance a Wavelength Electronics Model LFI-3526 Temperature Controller. This temperature controller 17 is connected to the DUVCH 15 for controlling the temperature therein.

An embedded stirring system (not shown) in the DUVCH 15 assembly provides a means to ensure even heating of the sample and to assist with the removal of air bubbles from the sample. Absent stirring, dissolved air or gas often comes out of solution and forms bubbles which interfere with the measurement.

The DUVCH 15 is connected also to a UV-visible light source (UV-vis LS) 14, such as for instance a Deuterium-Tungsten combination light source, and a spectrophotometer 16, such as a Rack Mount Ocean Optics spectrometer, via optical fiber cables (not shown) suitable for good transmission of light at 230 nm. The Uv-vis LS 22 irradiates the DUVCH 15 for obtaining a UV measurement of the liquid sample. The spectrophotometer 16 measures the UV light that is transmitted through the liquid sample. The optical system, i.e. the UV-vis LS 14 and the spectrophotometer 16 are controlled, for example, by Labview VI software.

The processor 18, the DUVCH 15, the temperature controller 17, the UV-vis LS 14, and the spectrophotometer 16 are placed within a constant temperature enclosure (CTE) 19, such as for instance a Hoffmann Enclosure with air conditioning for temperature control. The CTE 19 prevents the apparatus from being effected by unwanted fluctuations in the temperature. This is done to prevent possible damage to the processor 18 from excessive heat or humidity in industrial applications, such as in pulp and paper processing, and to obtain reproducible results. The CTE 19 is needed as in accordance with an embodiment of the invention because the response of spectrophotometer detector elements varies with temperature.

The data obtained by the spectrophotometer 16 is provided to the processor 18 for analysis and interpretation. The processor 18 provides a signal via a feedback circuit 22 to a process controller 21 of the process 5. The process controller 21 adjusts a process variable in dependence upon the feedback signal provided by the processor 18. For instance, a rate of addition of a chemical additive to the process 5 is modified to manage better the pitch deposition rate or the pitch tackiness. In this way, the present invention is suitable for performing continuous on-line monitoring of a process to measure a response to a chemical agent addition.

Figure 5:
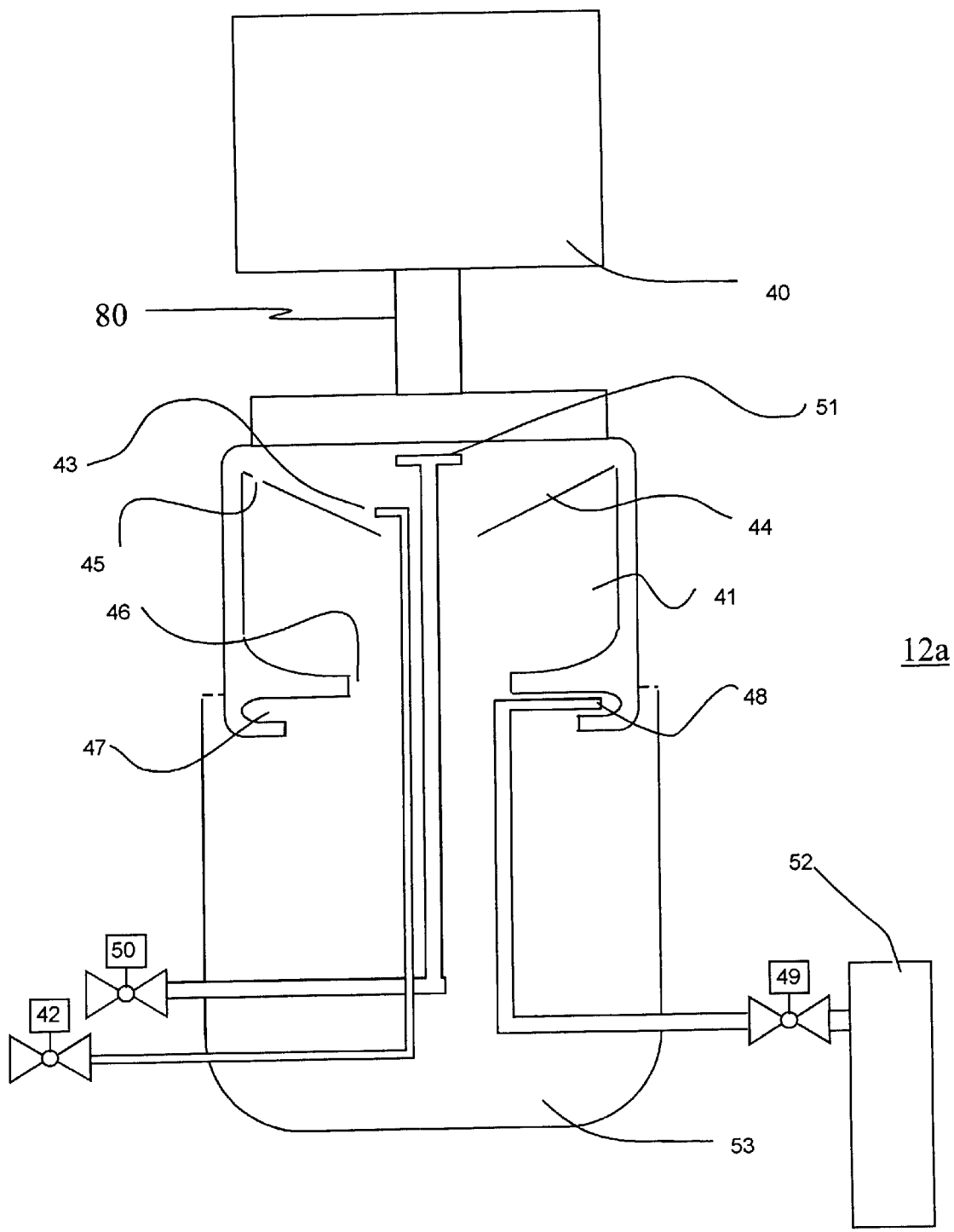
FIG. 5 shows a simplified block diagram of a centrifugal separation unit for use in the system of FIG. 4.

Referring now to FIG. 5, shown is a schematic block diagram of a centrifuge-based separation unit 12a for use in a first preferred embodiment of the present invention. In use, a variable speed motor 40 for driving the centrifugal separation unit is brought up to a predetermined speed. Power is transferred from the motor 40 to the centrifugal separation unit via a drive shaft 80. A liquid sample is introduced through automated valve 42 into a rotating centrifuge bowl 41 via a sample feed input tube 43. The valve 42 is in fluid communication with the SMCU 13 and with the sample manifold 11. Sample introduction is performed at a predetermined flow rate that is typically set at 80 ml/min using a flow regulator (not shown). The fill rate is optimized with respect to the settling rate of the particles or fiber that are to be removed prior to measurement. The sample emerges from the feed input tube 43 and drops onto the centrifugal entrance baffle 44. The sample flows along the entrance baffle 44 to the outer rim of the centrifuge bowl 41 with a minimum of agitation due to the low flow rate. The slope of the entrance baffle increases the settling efficiency since it introduces an additional surface for the particles to settle onto. At the outer edge of the entrance baffle the sample passes into the main centrifuge bowl through baffle exit slots 45. Large and heavy particles and fibers remain near the periphery of the bowl as it fills. The bowl fills radially inward until the level reaches the spill-over lip 46, at which point the liquid flows over the pick-up accumulator 47. The opening of the sample pick-up tube 48 is oriented opposite to the spin direction to capture and redirect the centripcally-separated fiber-free sample into the sample reservoir 52.

Once the reservoir is filled, the cleaning operation starts. The SMCU 13 closes the sample reservoir valve 49 and the sample inlet valve 42. As well, the SMCU 13 spins down the variable speed motor 40 to drain out through the drain accumulator 53. The cleaning operation consists of the SMCU 13 opening the fresh water valve 50 to allow pressurized fresh water to spray radially through the cleaning nozzle 51. The cleaning nozzle 51 is directed towards areas of highest accumulation, for example the entrance baffle 44, and along the bowl assembly 41 surfaces. The bowl assembly surface is machined to high precision to minimize the accumulation of debris. During the cleaning cycle the variable speed motor 40 executes a series of clock-wise (CW) and counter clock-wise (CCW) spin/stop cycles to provide agitation to purge any accumulation in the bowl. Fresh water valve 50 is closed by the SMCU 13. The variable speed motor 40 is brought to a full stop to allow complete drainage of the bowl assembly 41 and the sample accumulator 47.

Figure 6:
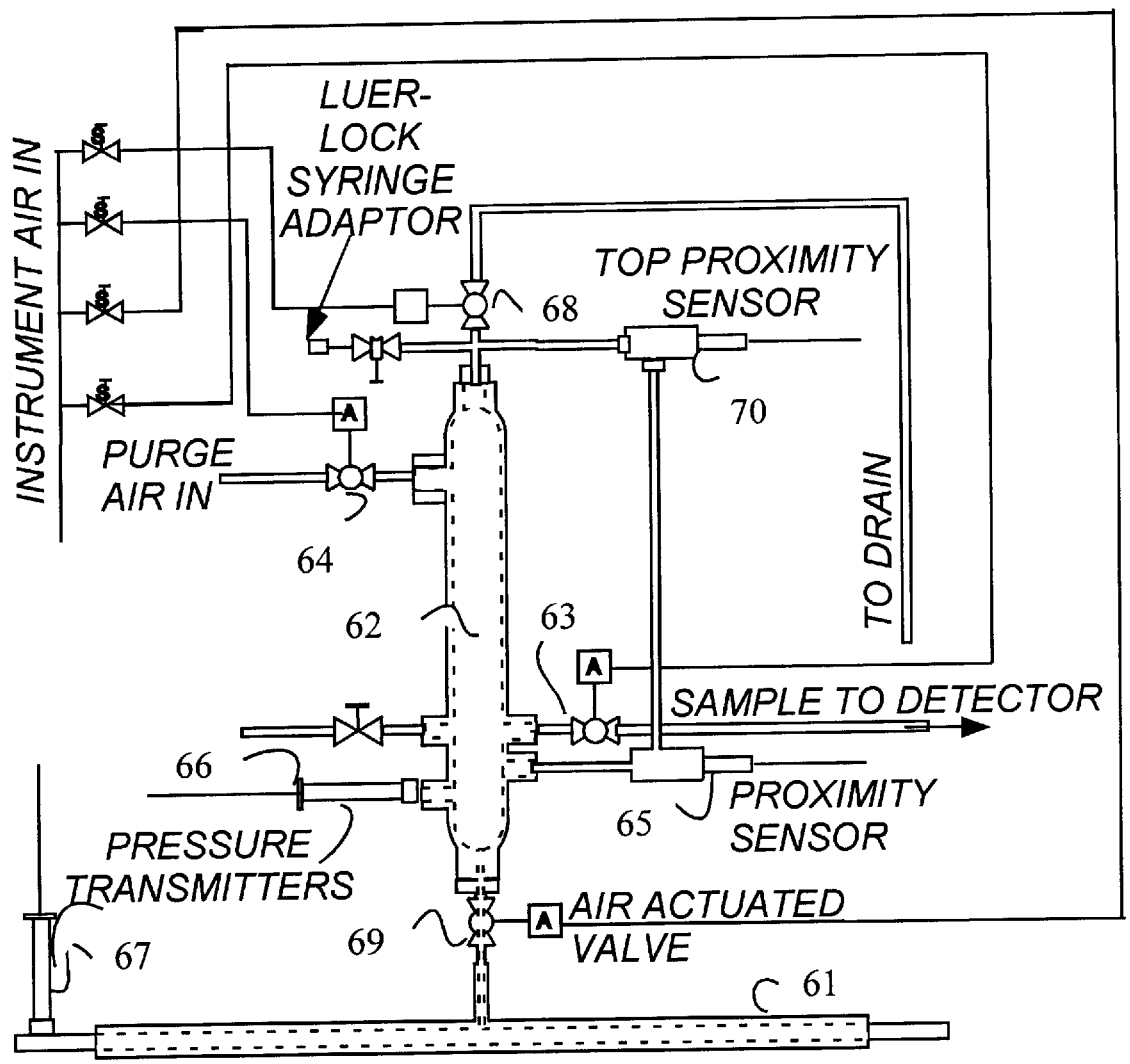
FIG. 6 shows a simplified block diagram of a filtration backflush unit for use in the system of FIG. 4.

Referring now to FIG. 6, shown is a schematic block diagram of a filter-based separation unit 12b for use in a second preferred embodiment of the present invention. The filtration and backflushing unit 12b provides a fiber-free liquid sample for optical analysis. The colloidal mixture is separated from the fiber by cross-flow filtration using a 5 or 10 micron Mott sintered metal filter 61. Tangential flow through the filter 61 is greater than 20 liters/minute and preferably >40 liters/min. The flow across the filter 61 is 10–200 ml/minute. The backflushing unit allows a reservoir 62 to fill with filtrate. Then the sample valve 63 is opened for 2 seconds to deliver 1–20 ml of colloidal sample to the DUVCH 15. The sampling period is followed by a delay period during which the filter 61 is closed and temperature dependent UV measurements are made by the spectrophotometer 16 using the recently obtained sample. After the measuring delay the reservoir 62 is purged by opening an air valve 64 (labeled purge air in) and backpulsing the filtrate backwards through the filter 61 for a specified period of at least 1 second but no longer than until the filtrate reaches the bottom proximity sensor 65. Backpulse pressure at pressure transmitter 66 is preferably greater than normal pressure measured at pressure transmitter 67. The bottom proximity sensor 65 relays a signal to the system controller/processor 18 to close the purge air valve 64 and open the reservoir vent valve 68. At this point the filter valve 69 is opened and the reservoir 62 fills until the top proximity sensor 70 detects the filtrate. The full sample valve 63 immediately opens to obtain another sample of the colloid material.

Figure 7:
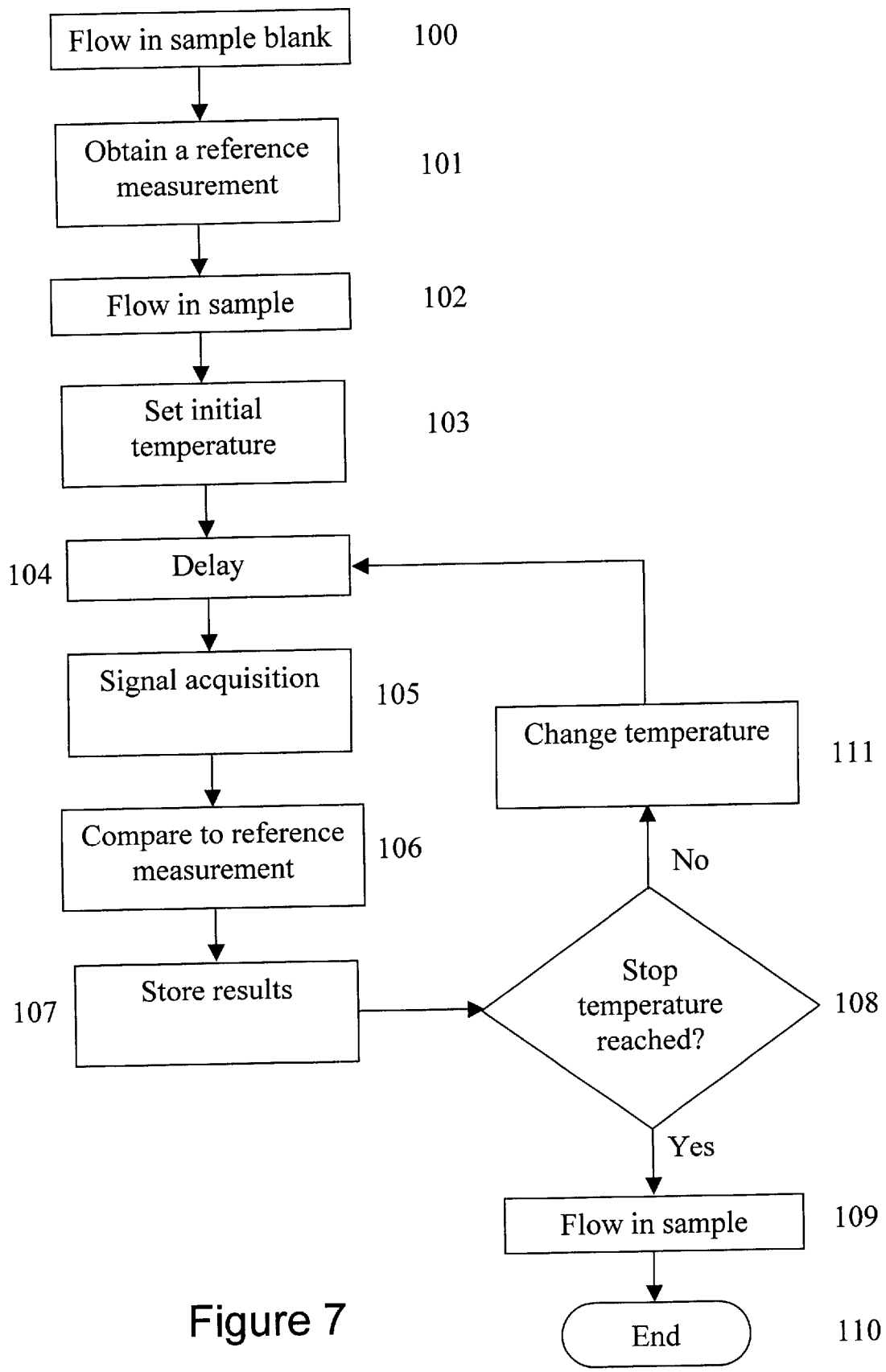
FIG. 7 shows a simplified flow diagram of a method for data acquisition using the system of FIG. 4.

Referring now to FIG. 7, shown is a simplified flow diagram of a method for performing a routine analysis of a fiber-free sample of process water according to the present invention. At step 100 the DUVCH 15 is charged with a sample blank, for instance distilled water, by the SMCU 13. A reference measurement, in the form of an intensity spectrum of the sample blank, is obtained at step 101. At step 102 the sample blank is flushed from the DUVCH 15 and the DUVCH 15 is charged with fiber-free sample by the SMCU 13. The initial temperature of the sample is set at step 103 and the sample is allowed to change to said initial temperature during a delay period that is introduced at step 104. At step 105 a light attenuance measurement at a predetermined wavelength of light is obtained. At step 106 the reference spectrum that was previously obtained at step 101 is subtracted from the signal. The base-line subtracted results are stored at step 107. If at decision step 108 it is determined that the stop temperature has been reached, then the sample is flushed from the DUVCH 15 by the SCMU 13 at step 109 and the method of FIG. 7 is terminated at step 110. If the stop temperature has not been reached at step 108, then the sample temperature is changed by a predetermined increment at step 111 and the steps 104 through 108 are repeated in sequence.

The results that are obtained using the method of FIG. 7 are in the form of a series of ultraviolet light attenuance values for a same colloidal mixture, each value corresponding to the colloidal mixture at a different temperature. The change in the light attenuance as a function of temperature at a single wavelength, an amount referred to as A, provides a measure of the thermal stability of the pitch particles. When a mixture of colloidal pitch is heated up, portions of the pitch particles dissolve into the aqueous phase. The size-distribution of the particles also changes thereby reducing the turbidity or scattering due to the particles. The variation in the light attenuance, for instance the combination of light absorbance of particles and surrounding medium and light attenuation due to scattering, is substantially different at different wavelengths. The wavelength dependence of the UV-visible difference spectrum taken at different temperatures provides information related to the absorbance of the species released from the colloidal pitch particles.

Figure 8:
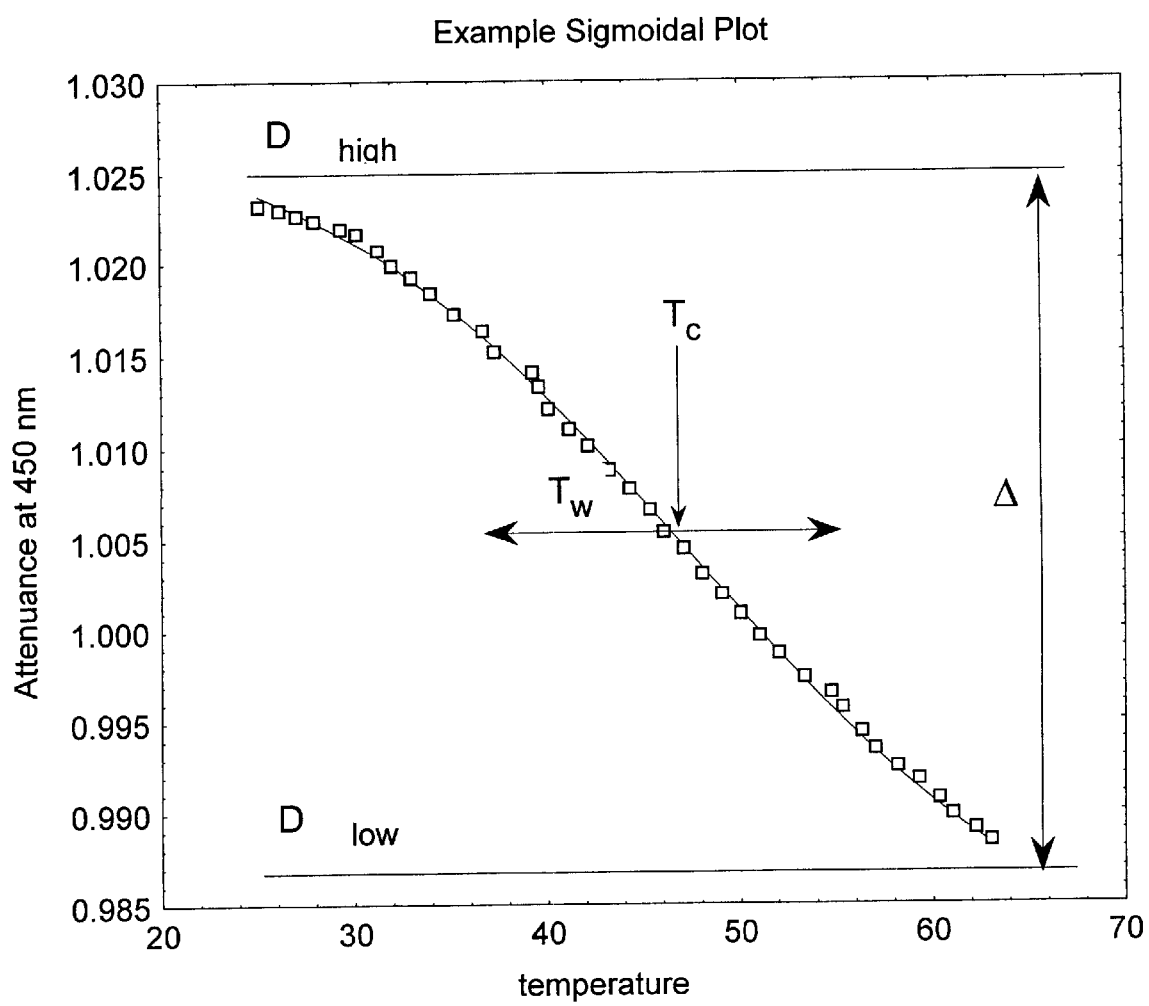
FIG. 8 presents an example plot of light attenuance by a colloidal mixture at one wavelength as a function of temperature.

Referring to FIG. 8, shown is a typical experimental plot of the light extinction at a single wavelength versus temperature, obtained using the method of FIG. 7. The thermal response of the pitch is nearly always sigmoidal in shape, and the analysis includes fitting the data with sigmoidal functions. The characteristic factors are a high attenuance $D_{high}$, a low attenuance $D_{low}$, a central temperature $T_c$, a width $T_w$ and the difference between high and low attenuance delta ($\Delta$). We have observed that these variables provide important clues to the stability of the pitch suspension. The increase of $T_c$ and decrease of $T_w$ and delta ($\Delta$) are indications of the greater stability of suspended pitch. Temperature variation spectroscopy utilizes molecular probes of the stability of pitch particles to assess pitch tackiness. As pitch particles are heated they decrease in size and components are ionized.

Figure 9:
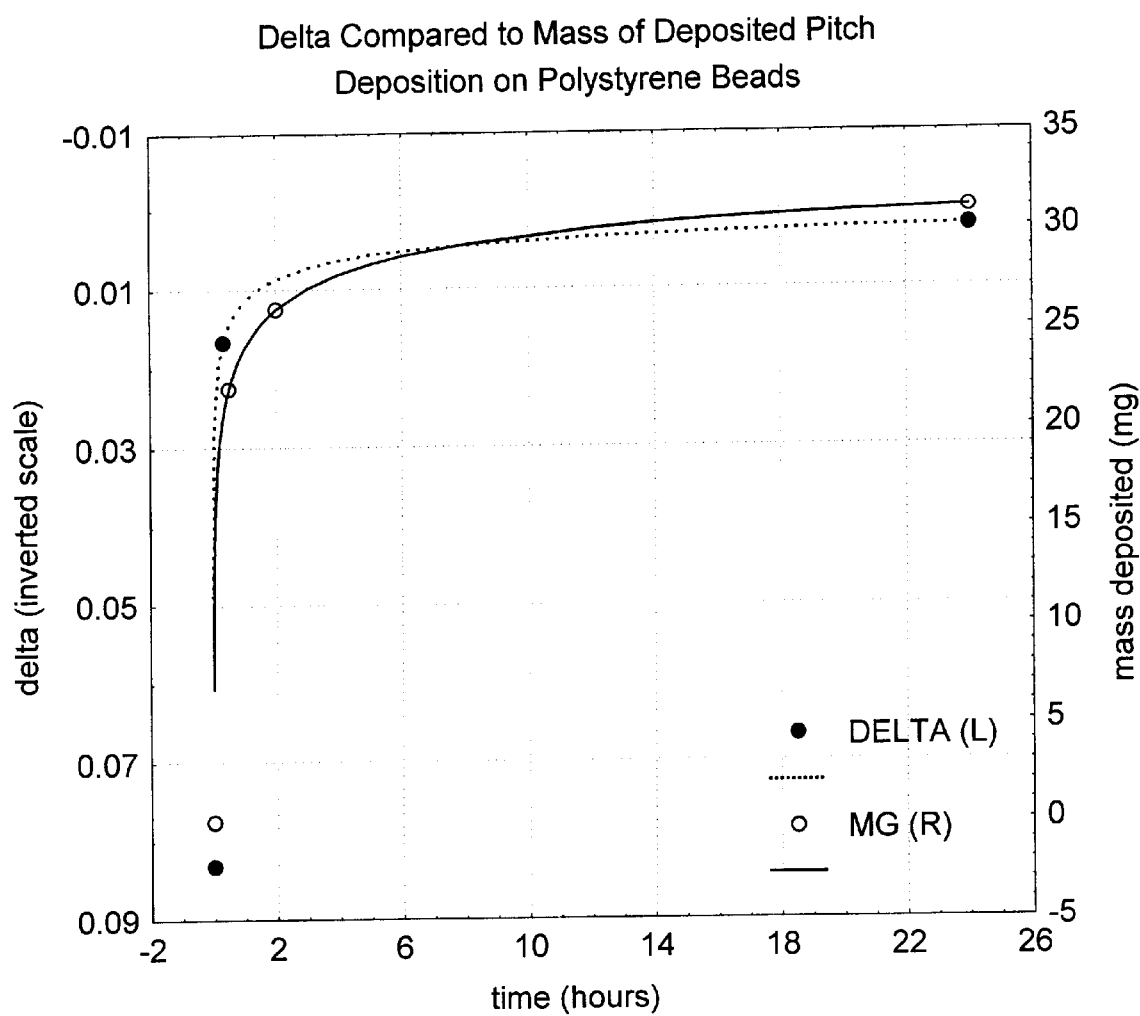
FIG. 9 presents a comparison of the delta value and the mass of deposited pitch as a function of time.

Referring now to FIG. 9 the value $\Delta$ may be related to, for example, the mass of pitch that may be deposited. FIG. 9 shows values (left axis, inverted scale) and mass of pitch deposited on 500 micron size poly(4-ethylstyrene-co-divinlbenzene) beads (right axis) as a function of time. Over time the pitch deposits on the beads, initially with a rapid deposition rate and later with a much slower deposition rate that quickly approaches a plateau. Correspondingly, the A value decreases proportionally over time, as the mass of depositable pitch that remains in the mixture decreases. This example demonstrates that the value of delta provides a measure of the propensity to deposit or the amount of pitch that will deposit. The amount will be different for different surfaces but will proportional to delta.

Figure 10:
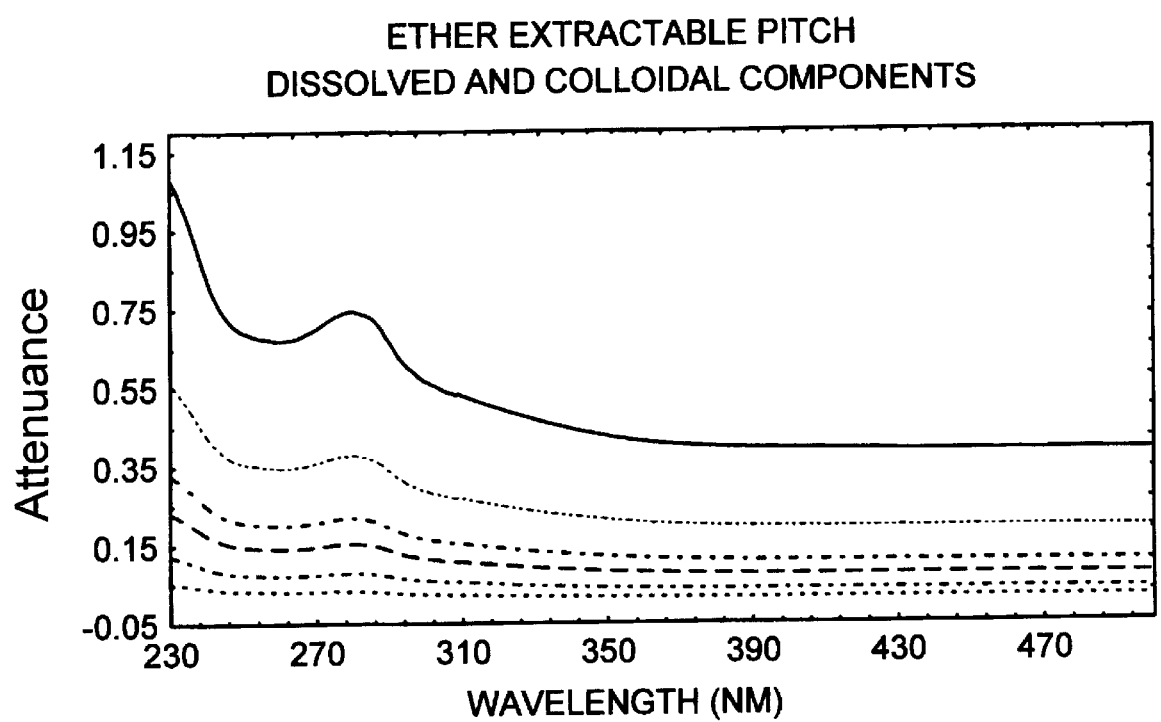
FIG. 10 presents the UV-visible spectra of dissolved and colloidal spruce/pine extractives at pH 5.4.
Figure 11:
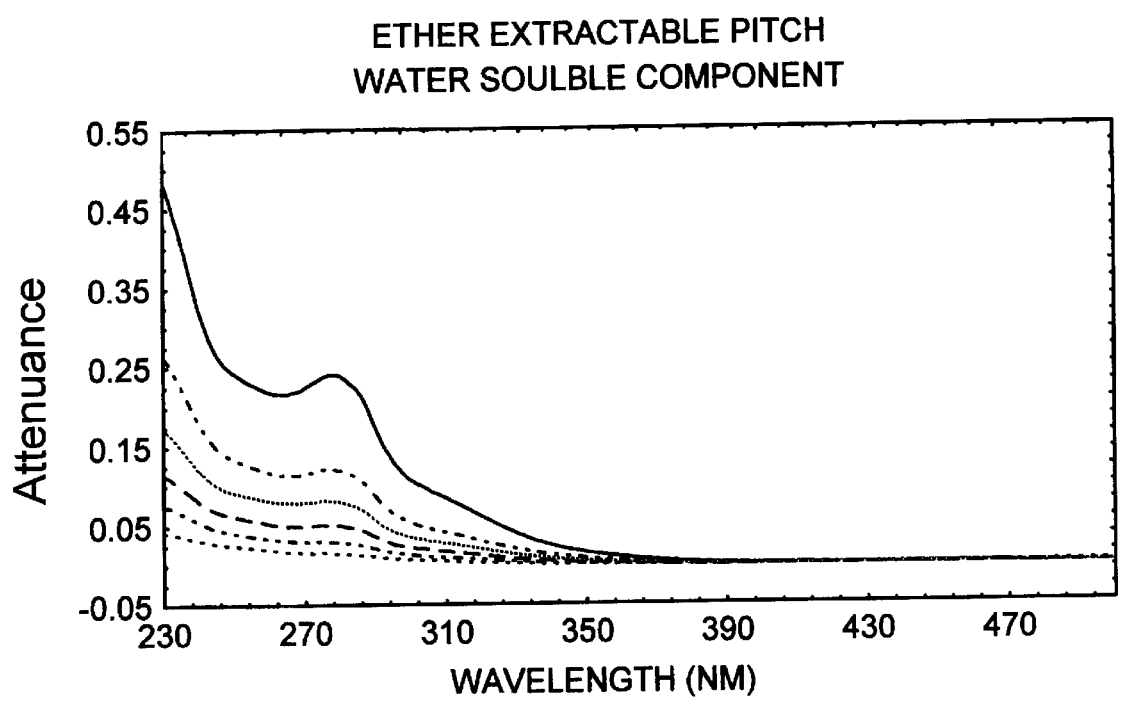
FIG. 11 presents the UV-visible spectra of dissolved spruce/pine extractives obtained by filtration of a colloidal mixture using a 0.45 micron filter.
Figure 12:
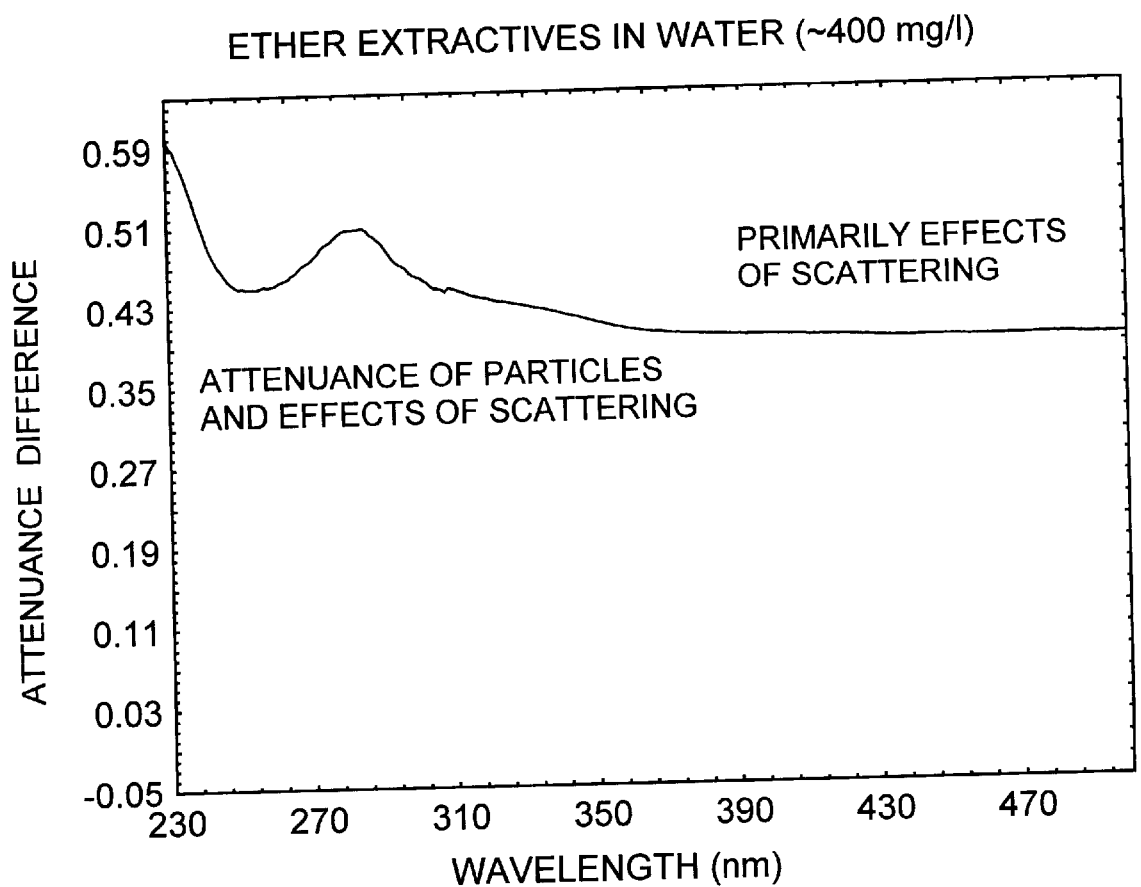
FIG. 12 shows the UV-visible difference spectrum isolating the attenuance of the colloidal pitch.

The existence and characteristic temperature of the phase transition is sufficiently important to the technique that the description of these properties becomes an object of the invention. Hence, in order to identify or measure the colloidal mixture it is important to determine a suitable temperature range and wavelength to obtain measurements. Typically these determinations are performed only once, for instance during initial set-up of the system hardware and software at a particular installation site. For example, a t-butyl ether extract of wood resin is obtained by successive extraction of a sample of white water obtained from a spruce/pine thermomechanical pulp mill. The extract is concentrated and then the resin is redispersed in pH 4.85 acetic acid aqueous buffer solution by sonication. A stock mixture comprising the dissolved and colloidal wood resin is diluted with buffer to six different concentrations. A series of UV-visible attenuance spectra that were obtained directly from these colloidal mixtures at room temperature are presented in FIG. 10. The signal from dissolved and colloidal matter followed the expected linear relationship with concentration. Additionally, the six colloidal mixtures of different concentration are filtered separately through a 0.45 micron syringe filter to obtain corresponding solutions absent the colloidal wood resin component. UV-visible spectra obtained from these colloid-free mixtures are presented in FIG. 11. The attenuation of the signal due to the colloidal substance alone is obtained by subtraction of the signal from the filtered and unfiltered samples. An example for this is presented in FIG. 12. In FIG. 12, the signal above 350 nm is taken to primarily represent turbidity or attenuation of the light due to the Mie scattering by the particles. The peaks at 230 and 280 nm indicate that the chromophore containing wood extractives in the colloidal particles adsorbs light.

Figure 13:
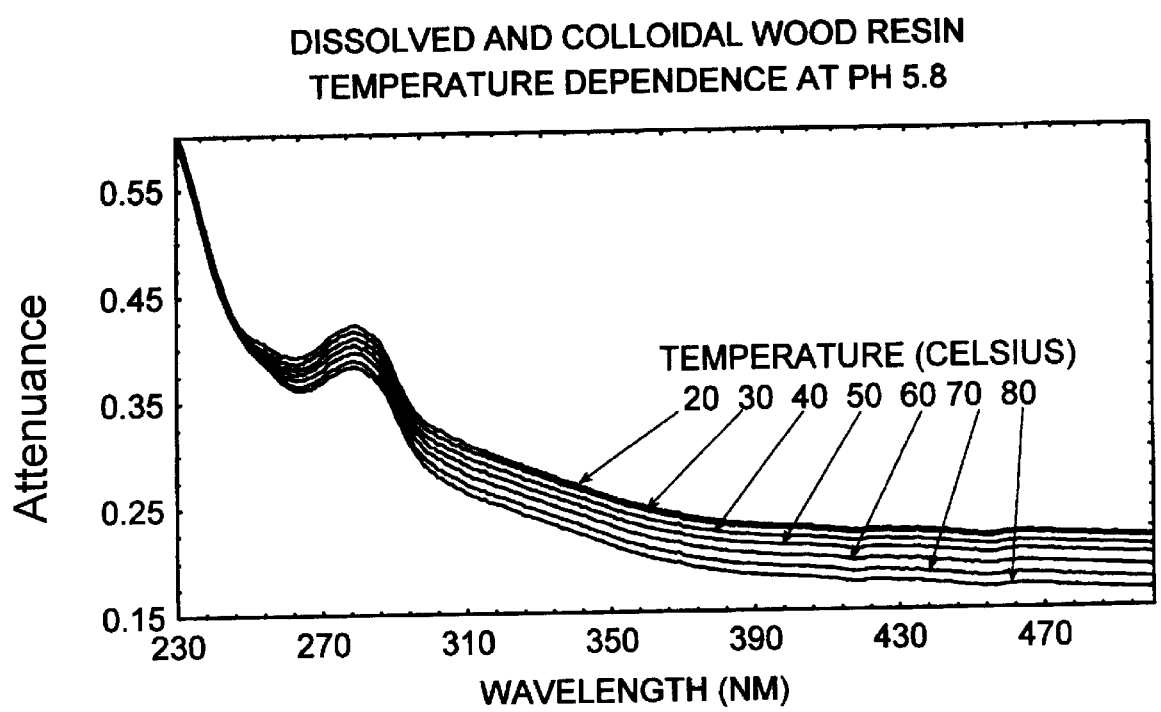
FIG. 13 shows the UV-visible spectra of dissolved and colloidal pitch at pH 5.8 and at different temperatures.

The temperature dependence of wood resin colloidal mixtures was characterized at different pH values, ionic strengths values, and with different amounts of clay relative to pitch. An example of the temperature dependence of the UV-visible spectrum of wood resin colloid mixtures is shown in FIG. 13.

Figure 14:
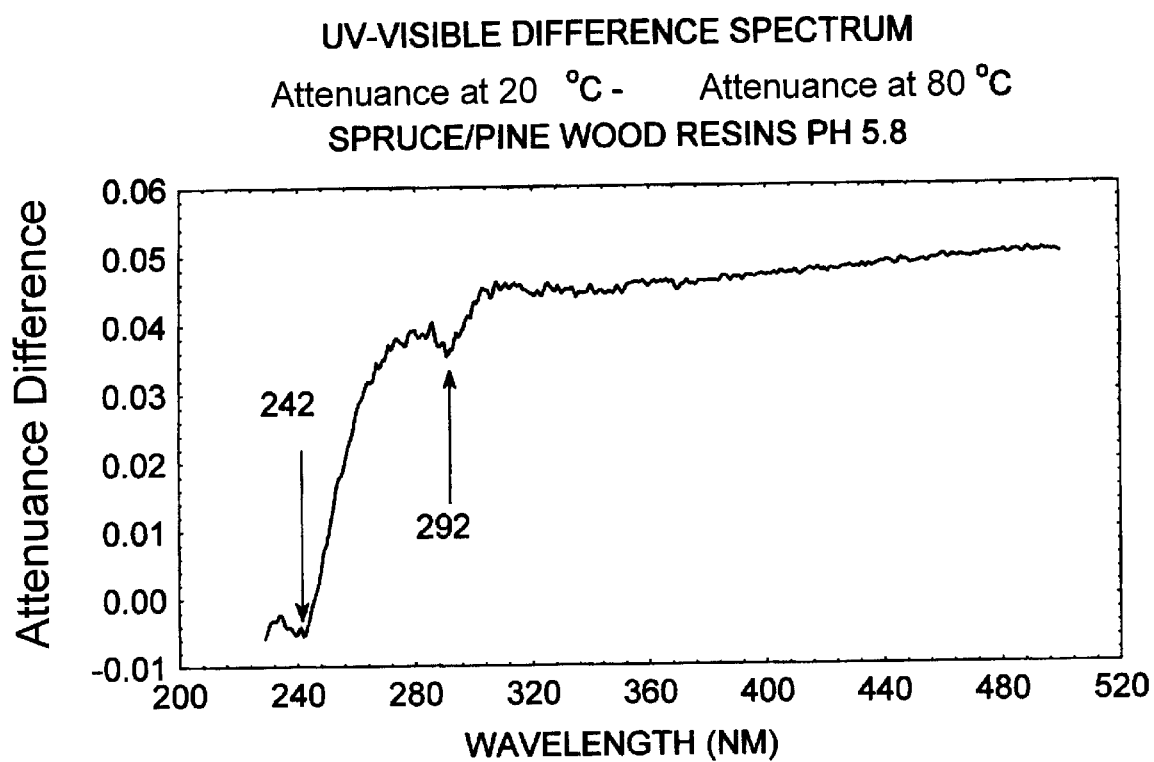
FIG. 14 shows the UV-visible difference spectrum showing the difference between the attenuance at 20° C. and 80° C.
Figure 15:
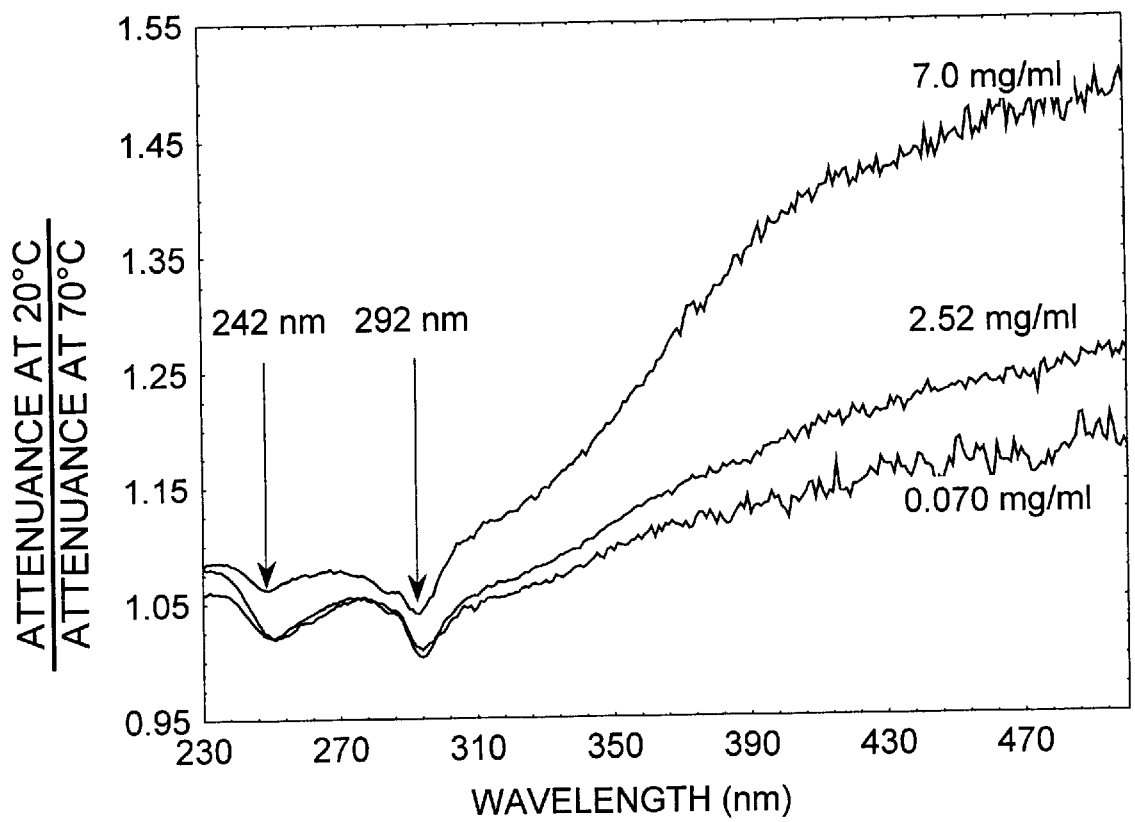
FIG. 15 shows a comparison of UV attenuance at different temperatures compared as ratios.

The wavelength dependence of the temperature variation of the UV-visible spectrum can be examined as one of a difference and a ratio of the spectra obtained at two wavelengths, as is shown in FIG. 14 and FIG. 15, respectively. Both methods show similar features. In the UV region the changes due to a decrease in scattering are compensated to varying degrees by an increase in the concentration of dissolved, UV absorbing species In order to perform a colloid concentration measurement according to the teachings of the present invention, an imposed temperature change must significantly perturb an equilibrium between dissolved and colloidal components of the mixture under investigation. Further the solution of dissolved molecules and the mixture of colloidal components must have optically measurably different properties, including molar absorptivity and the complex refractive index of the colloids and the solution. The nature of the suspended material and the solution conditions determine if such a phase change does occur; the temperature range and wavelength must be selected to best measure the phase change of a particular mixture. The optimal wavelength is selected by choosing a maximum or minimum from the difference or ratio of two spectra that are obtained for a same mixture at two different temperatures, as was described previously with reference to FIGS. 14 and 15, respectively.

Figure 16A:
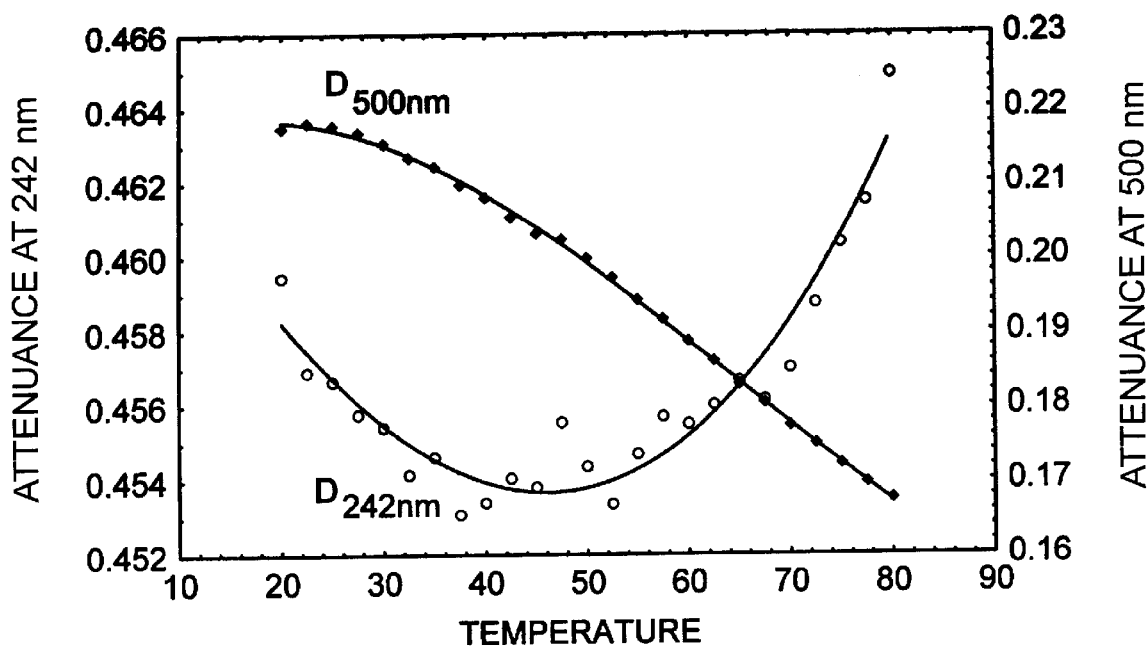
FIG. 16a presents a plot showing the temperature dependence of the UV-visible attenuance at two wavelengths.
Figure 17:
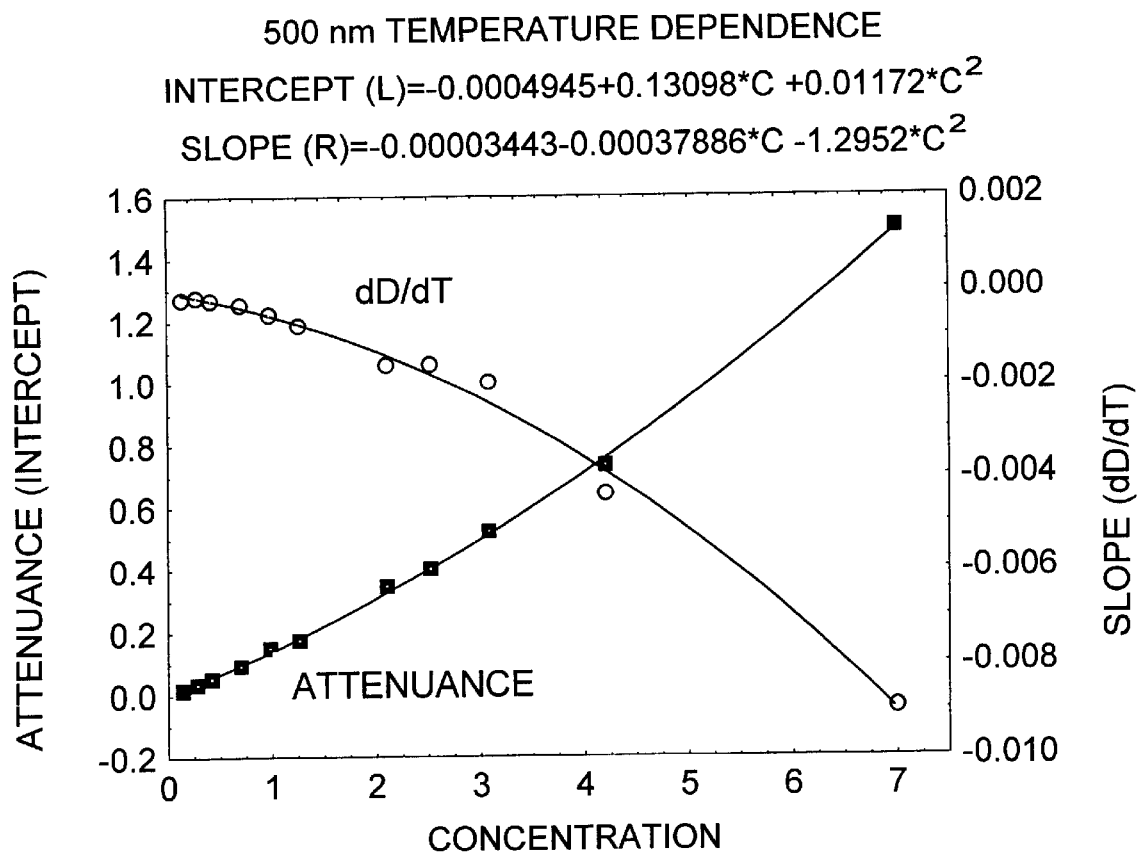
FIG. 17 shows a plot depicting the concentration dependence of the slope (dD/dT) and intercept from a linear regression of the attenuance of a wood-resin suspension obtained at 500 nm and the temperature.

The temperature dependence of the UV attenuance of the extracted pitch is plotted for two wavelengths in FIG. 16a. The variation at the 242 nm minimum in the difference spectrum shown in FIGS. 14 and 15 amounts to less than 3% of the total attenuance at that wavelength. On the other hand, the variation at 500 nm is approximately 25% of the attenuance at that wavelength. The variation of the attenuance at 500 nm is substantially linear with changes in temperature ranges between 40° C. and 80° C. It is within this linear region that two measurements provide a slope (dD/dT) that is proportional to the concentration of colloidal pitch. The slope ($dD_{500}/dT$) and intercept $$\left(\lim_{temperature \to 0} D_{500}\right)$$

are calculated from the temperature dependence of multiple concentrations of colloidal pitch. The slope (dD/dT) and the intercept plotted against the relative concentration are shown in FIG. 17. These original results demonstrate, for the first time, that the temperature variation of the attenuance or turbidity of colloidal pitch is proportional to the amount of pitch in the mixture. The results showing the variation of the intercept with concentration confirm the expected result that the turbidity is a function of the colloid concentration. Measurements are normally made in the concentration region that produces dD/dT values between 0.0 and −0.0025.

Figure 16B:
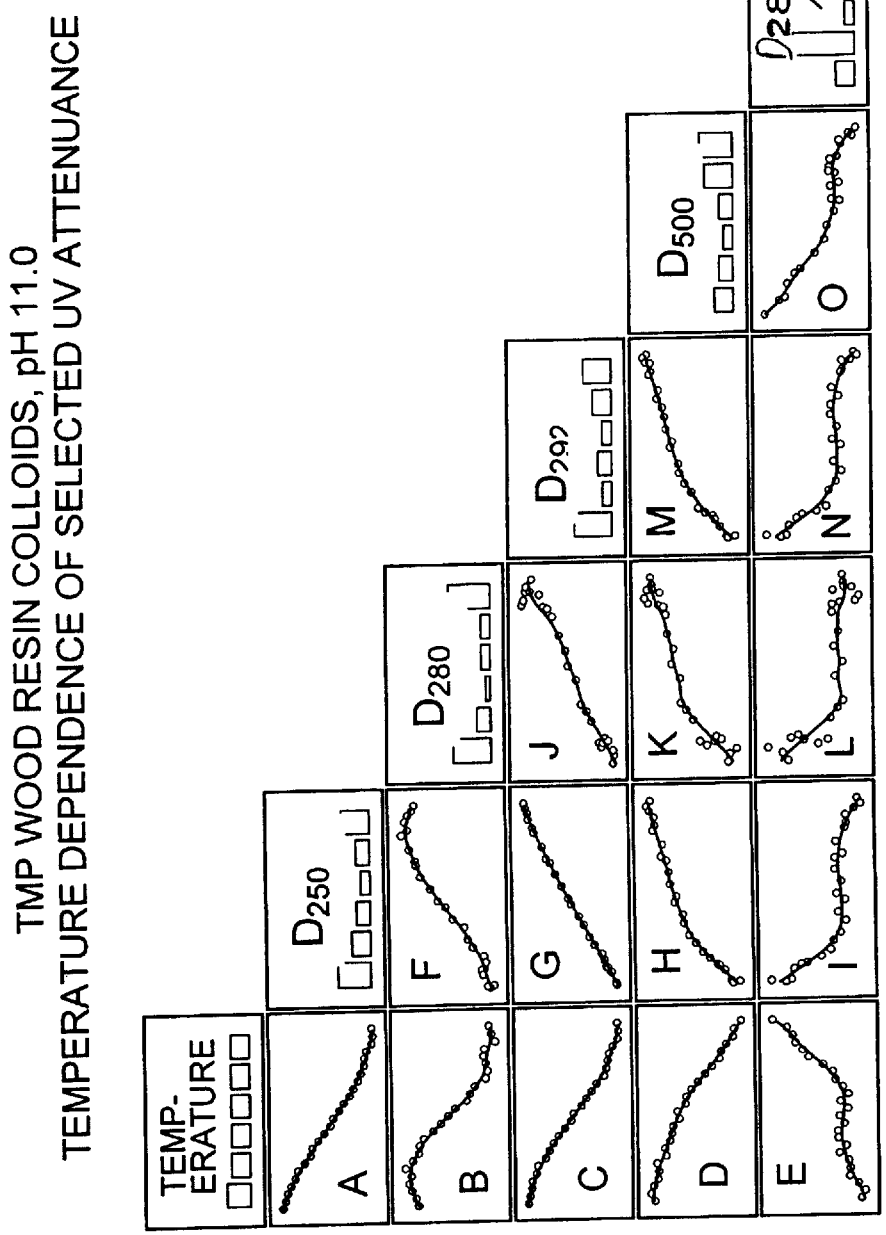
FIG. 16b presents a matrix plot showing the temperature dependence of the UV-visible attenuance of a mixture of wood-resin dissolved and colloidal substances at pH 11.
Figure 16C:
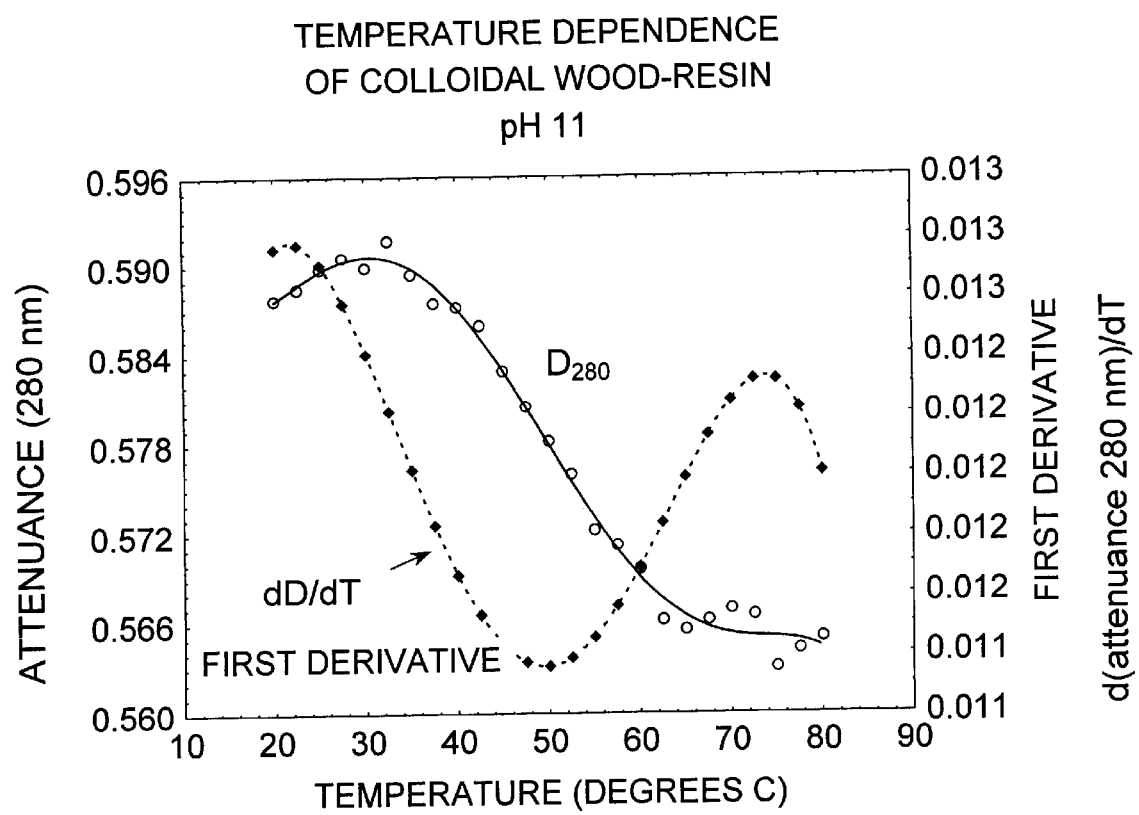
FIG. 16c presents a plot showing the UV attenuance at 280 nm versus temperature showing the first derivative attenuance-temperature relationship.

The optimal temperature range for measuring the property of the colloidal mixture is chosen by identification of a temperature region around a zero point in the second derivative of the attenuance with respect to temperature. FIG. 16b shows a matrix plot of the temperature variation of the UV attenuance at pH 11.0. Plots A–D show a variation in the shape of the curves of the attenuance at different wavelengths with respect to temperature (abscissa). At this mixture there is a relatively complete transition between the dissolved and colloidal components. In particular, the slope falls off significantly at the temperature extremes for the attenuance values at 280 nm. Plot D in FIG. 16b is examined in more detail in FIG. 16c. Inspection of FIG. 16c indicates that two measurements made in the region between 20° C. and 40° C. would give different results than measurements made between 40° C. and 60° C. The best region to measure the transition between the colloidal and liquid state is selected from the region where the slope is most constant. This occurs around the central point in the transition that is defined by the minimum in the first derivative function plotted in FIG. 16c. This minimum in the first derivative is the zero point in the second derivative function that occurs, for the data shown in FIG. 16c at 50° C. Secondary zero points in the second derivative occur around 23° C. and 74° C. but these are small regions with very small changes in the attenuance.

The matrix plot presented in FIG. 16b provides further means for the identification of phase changes in colloidal mixtures. In six plots (F, G, H, J, K, M) the attenuance at one wavelength is plotted against another. The linear relationship in plot G shows that the component which provides the dominant temperature variation contributes to both of these wavelengths at all temperatures. Plot H, on the other hand shows that the relative change in attenuance is linear in two regions, but the relationship appears to change in an intermediate region. The relative attenuance at two wavelengths may be captured in a ratio as is plotted against temperature in plot E. At the simplest level the ratio of attenuance values provides a means to inspect the relative change in one component with respect to the change in another component. The linear region with little slope in the central portion of the plot corresponds to a temperature region where changes in the attenuance at 500 nm directly correspond with a change in the attenuance at 280 nm.

Figure 18:
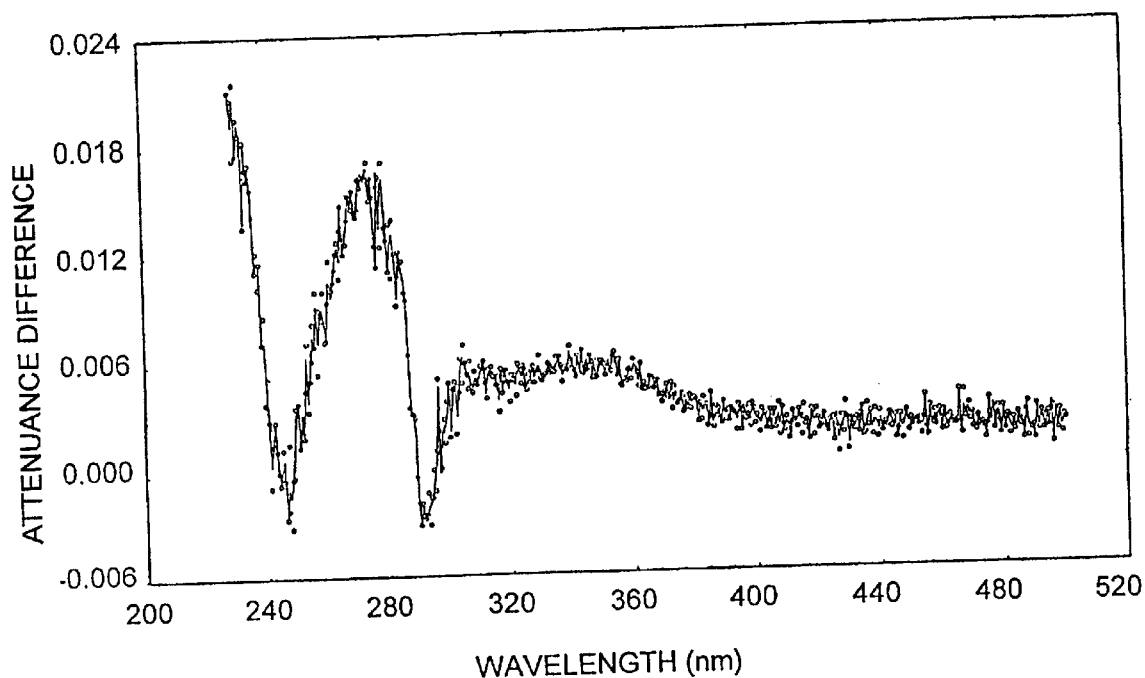
FIG. 18 shows a UV-visible difference spectrum from TMP (thermomechanical pulp) white water.
Figure 19:
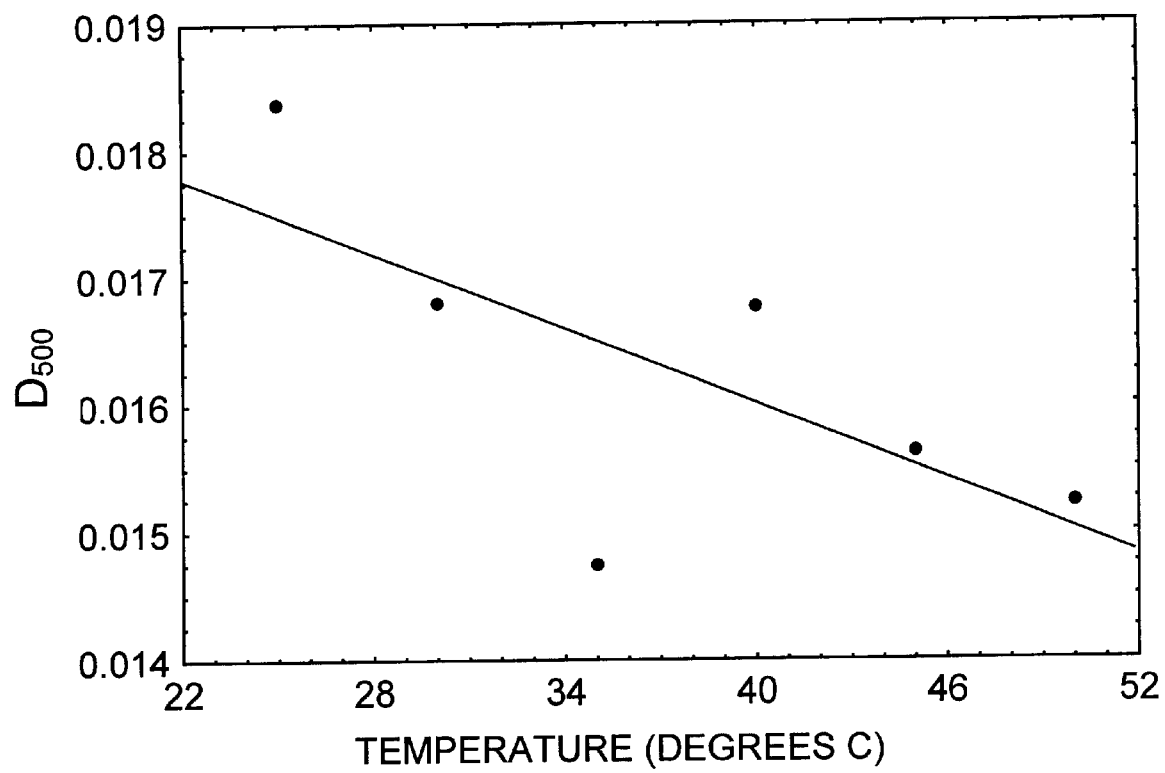
FIG. 19 shows a plot depicting the temperature dependence of the attenuance of a TMP white water at 500 nm.

Additional techniques to obtain accurate and reproducible measurements are learned through experience of applying these measurement techniques at a paper mill. Trial experiments were conducted at a paper mill using white water manually filtered on a Whatman 41 filter paper. This filter paper has a nominal size cut-off of approximately 20 microns. The results are exemplified by the difference spectrum in FIG. 18. This spectrum was obtained with a 1 mm UV cell on a Cary 1 spectrophotometer. This spectrum shows the same minimum points as the difference spectrum in FIGS. 14 and 15. However, in this case the relative attenuance at long wavelengths is much lower. The difference spectrum demonstrates that the temperature change necessary to get accurate measurements must be at least 30 degrees C. Furthermore, a long path UV cell (10 or 20 mm) is used to increase the accuracy of the measurements made at long wavelengths. Scatter in the mill data required to obtain dD/dT is shown in the FIG. 19.

Figure 20:
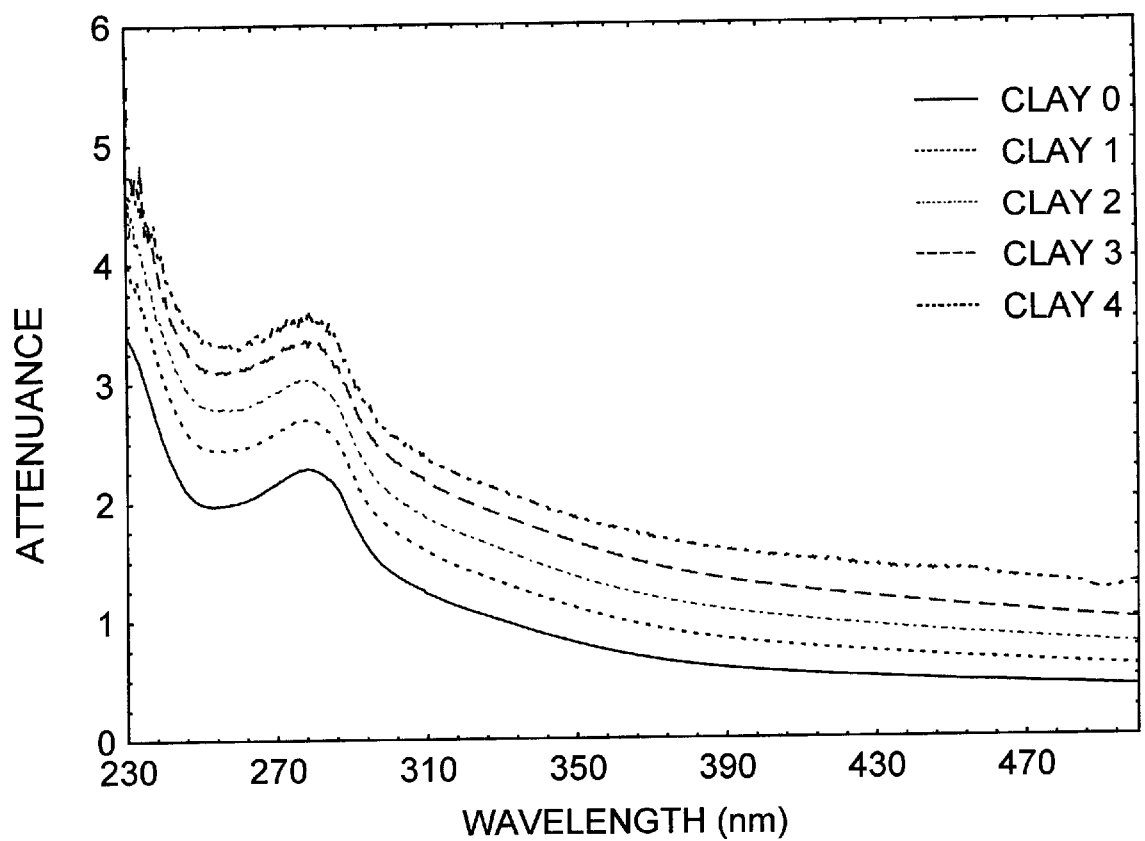
FIG. 20 shows UV-visible spectra of a colloidal mixture of wood-resin with different amounts of added clay.

FIG. 20 shows the spectral effects of adding multiples of a clay concentration to a colloidal pitch solution. The attenuance changes are nearly linear with clay concentration and relatively monotonic with wavelength. Clay and fillers scatter light well and absorb little light compared to colloidal pitch.

Figure 21:
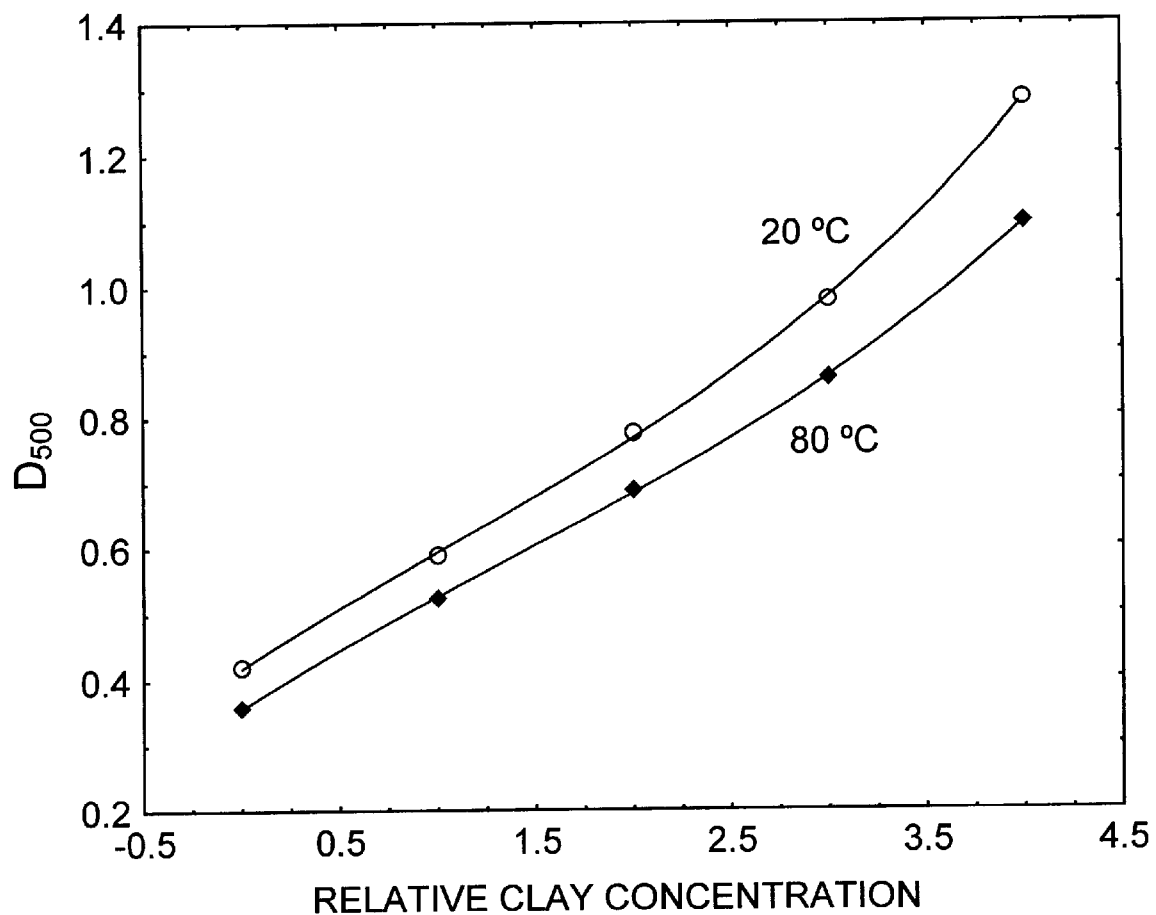
FIG. 21 presents a plot showing the relationship between clay concentration in a pitch/clay mixture and attenuance at 500 nm at two temperatures.

FIG. 21 shows attenuance at 500 nm for different concentrations of clay in a colloidal pitch mixture. The total attenuance is linear with clay concentration. The temperature variation, representing the constant amount of pitch, is shown by the gap between the attenuance at 20° C. and 80° C. Although the size of the gap appears to increase slightly at higher clay concentrations, it is relatively constant given the dramatic range in clay concentrations. Normal variation in clay or filler concentration in a paper mill is usually no more than a factor of two. The data in FIGS. 20 and 21 may be used with a measure of the temperature dependence to first calculate the total amount of the colloids and then calculate the amount of colloidal pitch and finally calculate the difference that constitutes colloidal clay and other components that are insensitive to transitions between the colloidal and dissolved phases in the measured temperature range.

In a paper mill situation, it is advantageous to make maximum use of carrying capacity of water resources and still minimize the risk of sudden or catastrophic wet-end chemistry events that lead to deposits and machine fouling associated with poor efficiency and runability. A measurement that provides the paper-maker a better means of predicting the sensitivity of the white water system upsets may be applied to circumvent expensive episodes of deposition on the paper machine. Among diverse causes of wet-end chemistry upsets the sudden variation in white water temperature leading to a wet-end upset is known among papermakers as temperature shock. A sudden change in white water temperature may occur when unusual quantities of fresh water are brought into the water system. In an embodiment, this invention provides a measure of the susceptibility of the water system to a temperature shock. In another embodiment in agreement with the invention concentrations of dissolved and colloidal substances that may lead to deposition events are identified. The intention of the papermaker is thus to avoid a metastable state where dissolved components may suddenly come out with a minor fluctuation in operating conditions.

Figure 22:
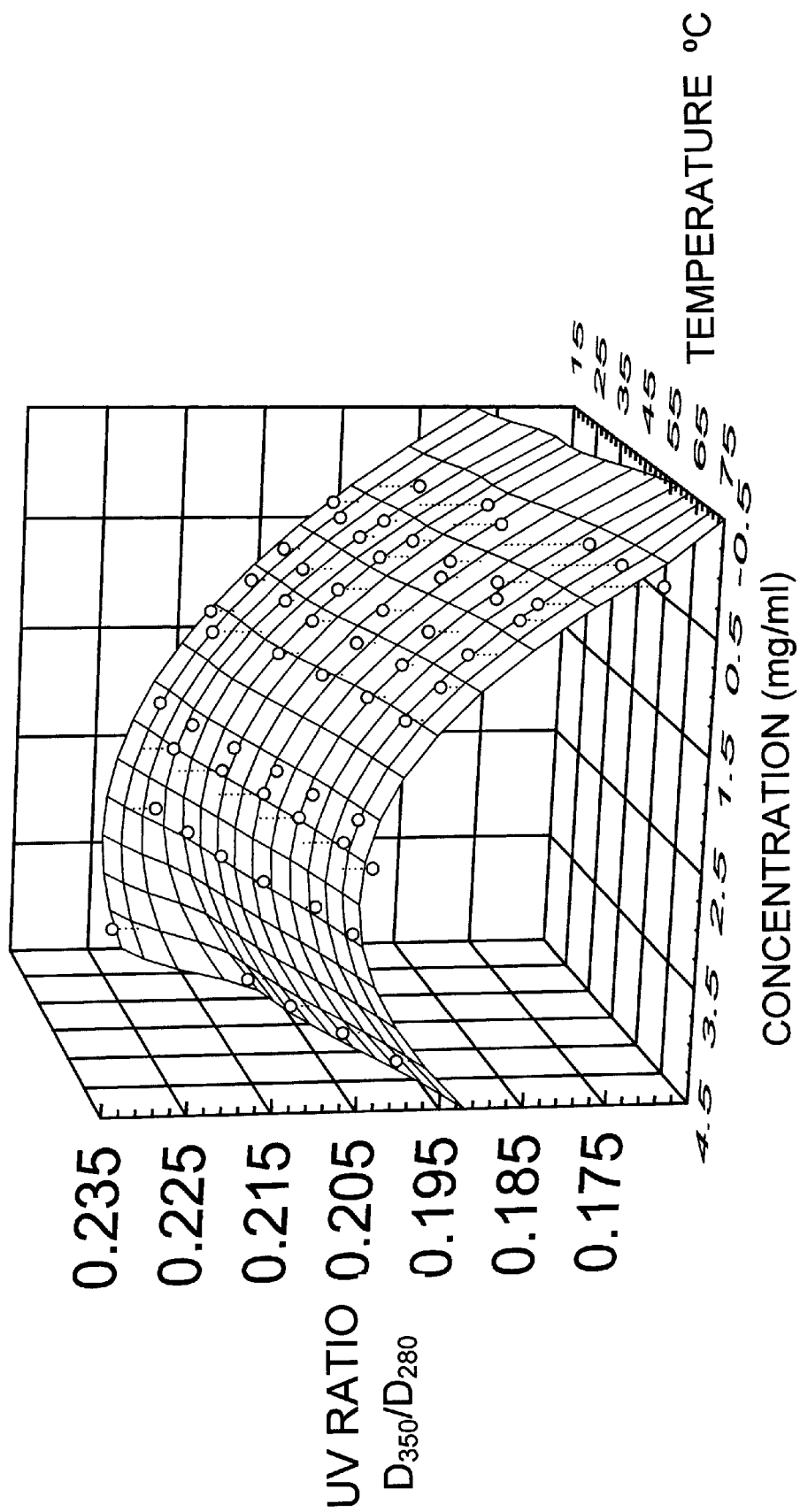
FIG. 22 shows a 3-D plot of the UV ratio $D_{350}/D_{280}$ versus temperature and concentration.
Figure 23:
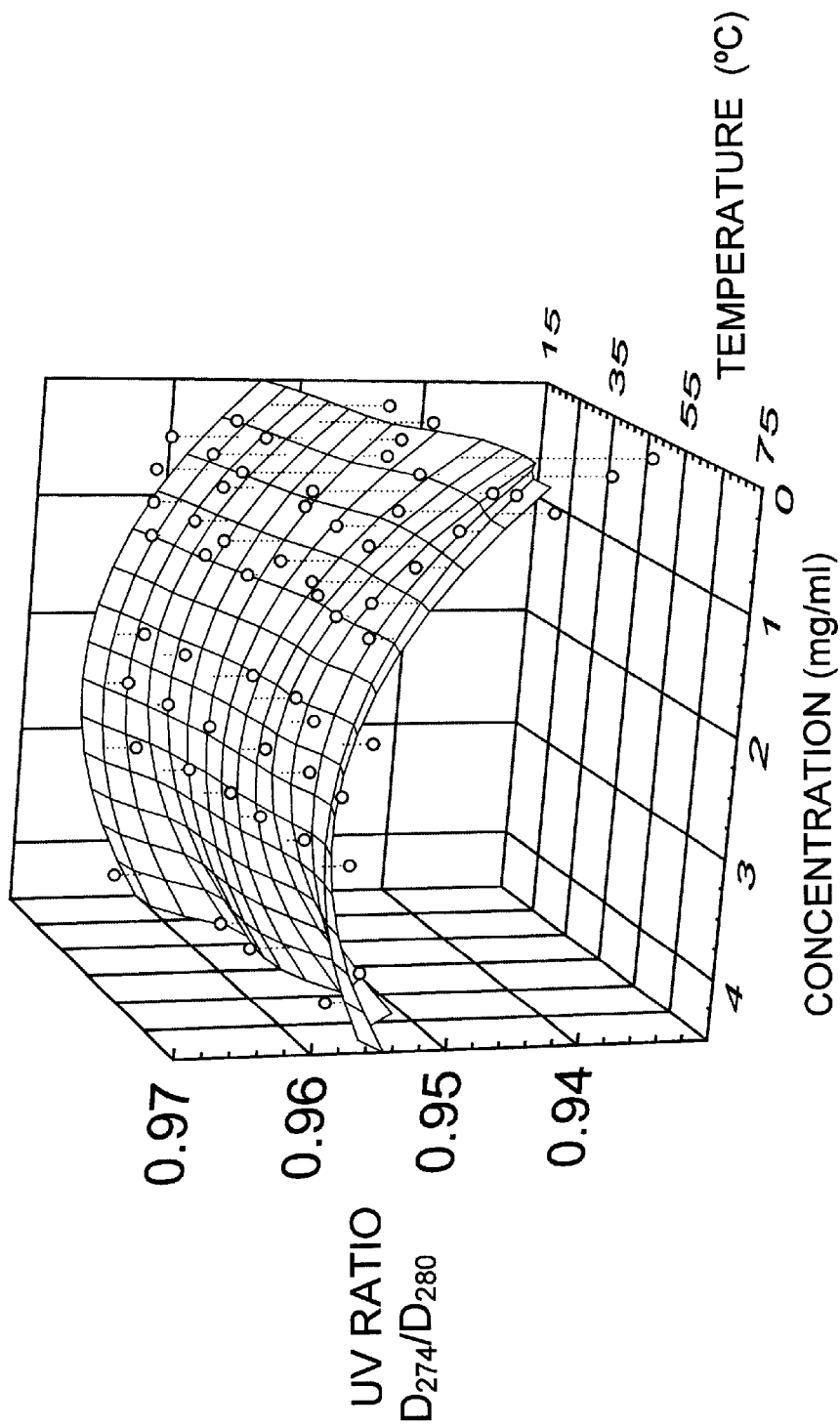
FIG. 23 shows a 3-D plot of UV ratios $D_{274}/D_{280}$ versus temperature and concentration (TDS)
Figure 24:
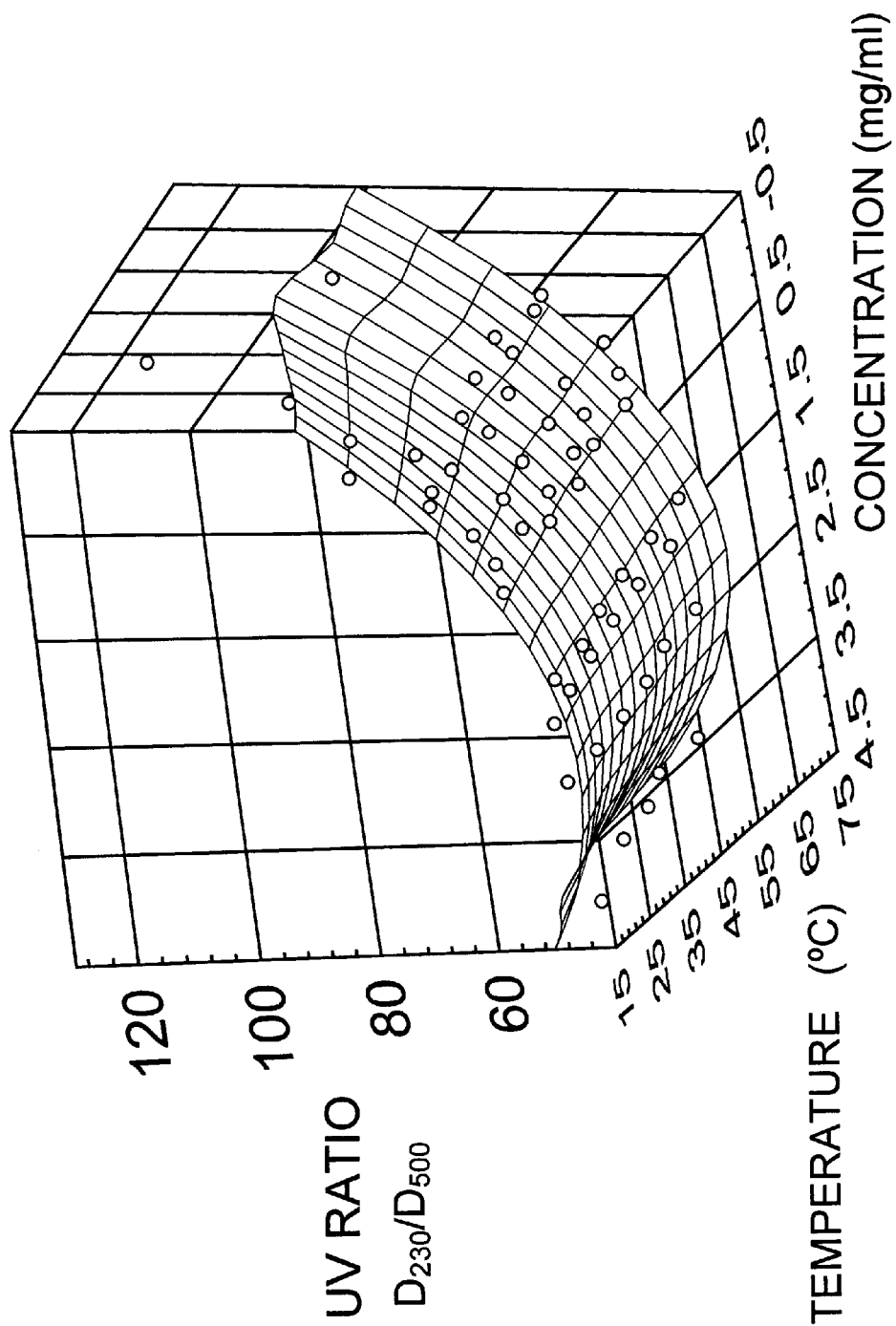
FIG. 24 shows a 3-D plot of UV ratios $D_{230}/D_{500}$ versus temperature and concentration (TDS); and, FIG. 25 shows a 3-D plot of UV ratios $D_{250}/D_{280}$ versus temperature and concentration (TDS).
Figure 25:
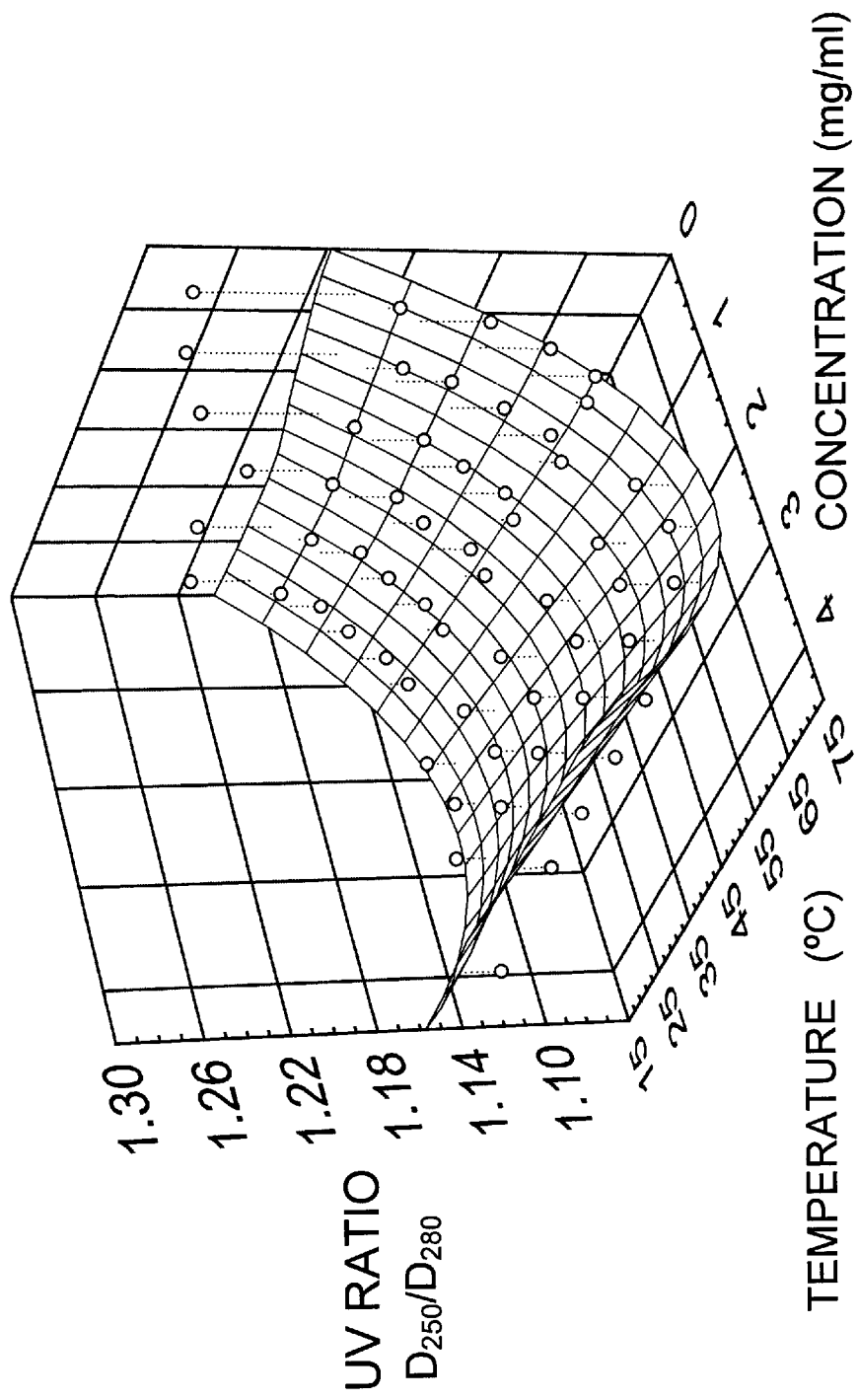

FIGS. 14, 15, 16b, and 18 demonstrate that the spectral changes that occur during pitch phase transitions are rich sources of information concerning the transitions that are occurring. Comparing attenuance values at different wavelengths provides a means of comparing the amount of one component to another component. Examples of three-dimensional plots of temperature, relative dissolved and colloidal substances are provided in FIGS. 22 to 25. Although for the most part UV-visible absorbance shows linear or nearly linear relationships with concentration (TDS) and temperature, the use of UV attenuance ratios provides insight into discrete changes in the state of the dissolved and colloidal substances. FIG. 22 shows the ratio $D_{350}/D_{280}$ versus temperature and concentration. The most pronounced change exhibited in this plot is below 1 mg/ml. The relative absence of slope in this graph at high temperatures suggests a change of state that is more discrete than the gradual change at low temperature. The UV ratio $D_{350}/D_{280}$ appears to be a comparison of the contributions of turbidity and UV attenuance. FIG. 23 shows UV ratios of $D_{274}/D_{280}$ versus temperature and concentration (TDS). At high concentrations this ratio is essentially constant. At low concentrations the ratio decreases. This is interpreted as a red shift due to the comparative effects of salvation in water versus solvation in pitch. FIG. 24 shows UV ratios of $D_{230}/D_{500}$ versus temperature and concentration (TDS). At high concentrations this ratio is essentially constant. Scattering adds proportionately to both long and short wavelengths. At low concentrations the ratio increases as more extractives are UV absorbing in the dissolved state but not colloidal. FIG. 25 shows UV ratios of $D_{250}/D_{280}$ versus temperature and concentration (TDS). At high concentrations this ratio is essentially constant indicating no substantial change in the ionization. At low concentrations the ratio increases as more extractives become ionized as they dissolve.

At concentrations above a critical concentration the UV ratio is essentially constant. Ratios that are important include ratios that emphasize ionization ($D_{250}/D_{280}$, $D_{300}/D_{280}$); solvent shifts ($D_{300}/D_{292}$) and a comparison between scattered and UV absorbed light ($D_{500}/D_{230}$). The attenuance at 292 nm ($D_{292}$) is essentially constant as a function of colloidal or dissolved state and therefore may be used to normalize measurements with respect to total concentration.

A scan of selected wavelength ratios versus temperature and identification of points at which the slope changes will identify temperatures that correspond to a transition between dissolved and colloidal components. These temperatures may be used as guides of the system stability at a different temperature.

Exemplary wavelength and temperature values for use with the apparatus of the instant invention have been provided above by way of specific example. Of course, those of skill in the art with a little experimentation can determine other embodiments with different values that work well. Further, varying conditions at different installation sites requires an initial calibration of the instrument to determine optimal wavelength and temperature values for use under the site-specific conditions.

Other examples of temperature sensitive equilibria between dissolved and colloidal substances that may be measured and controlled include: starch dissolution and retrogradation (setback), see for example TAPPI, *Starch and starch products in surface sizing and paper coating.* 2 ed, ed. H. W. Maurer. 2001, Atlanta: TAPPI PRESS. pp. 1–164; and, surfactant phase transitions.

The above-described embodiments of the invention are intended to be examples of the present invention and numerous modifications, variations, and adaptations may be made to the particular embodiments of the invention without departing from the scope and spirit of the invention, which is defined in the claims.

What is claimed is:

1. A method for controlling a characteristic of a colloidal mixture comprising the steps of:

providing a colloidal mixture for analysis by thermal difference spectroscopy;

determining a value indicative of the characteristic of the colloidal mixture by the steps of:

irradiating at least a first portion of the colloidal mixture with light in an ultraviolet-visible region at a first temperature and obtaining a first measurement of a first wavelength within the ultraviolet-visible region, said first measurement for obtaining a measure of one of an absorption, emission and scattering of the first wavelength when said colloidal mixture is irradiated with the light, waiting for the temperature of the colloidal mixture to change, irradiating at least a second portion of the colloidal mixture with light in an ultraviolet-visible region at a second different temperature and obtaining a second measurement of the first wavelength within the ultraviolet-visible region, said second measurement for obtaining a measure of one of an absorption, emission and scattering of the first wavelength when said colloidal mixture is irradiated with the light, and determining the value indicative of the characteristic of the colloidal mixture from a relationship including the first measurement and the second measurement;

determining, in dependence upon the determined value, an adjustment to at least a variable of a control process for affecting at least a characteristic of the colloidal mixture;

providing a feedback signal in dependence upon the determined adjustment to an automated controller of the control process; and adjusting automatically the variable of the control process in dependence upon the provided feedback signal.

2. A method for controlling a characteristic of a colloidal mixture according to claim 1, wherein the first portion and the second portion is substantially a same portion.

3. A method for controlling a characteristic of a colloidal mixture according to claim 2, wherein the characteristic of the colloidal mixture is one of colloid tackiness and colloid propensity to deposit.

4. A method for controlling a characteristic of a colloidal mixture according to claim 2, wherein the colloidal mixture includes a plurality of colloidal particles and wherein the characteristic of the colloidal mixture is a determinant of a size distribution of the colloidal particles.

5. A method for controlling a characteristic of a colloidal mixture according to claim 3, wherein the substantially a same portion is an approximately fiber-free portion of the colloidal mixture.

6. A method for controlling a characteristic of a colloidal mixture according to claim 5, wherein the approximately fiber-free portion of the colloidal mixture is provided using an in-line centrifuge unit.

7. A method for controlling a characteristic of a colloidal mixture according to claim 6, wherein the in-line centrifuge unit operates in a batch mode.

8. A method for controlling a characteristic of a colloidal mixture according to claim 6, wherein the variable of the control process is a rate of addition of a chemical additive for affecting at least a characteristic of the colloidal mixture.

9. A method for controlling a characteristic of a colloidal mixture according to claim 8, wherein the chemical additive is one of a dispersant, a coagulant and an adsorber.

10. A method for controlling a characteristic of a colloidal mixture according to claim 9, wherein the colloidal mixture includes a temperature sensitive component and a temperature insensitive component.

11. A method for controlling a characteristic of a colloidal mixture according to claim 3, wherein a difference between the first temperature and the second different temperature is at least 30° C.

12. A method for controlling a process parameter of a process involving a colloidal mixture comprising the steps of:

providing at least a first portion of the colloidal mixture for an optical measurement by the steps of:
providing a portion of the colloidal mixture to an in-line centrifuge unit to separate particulate matter therefrom, to obtain an approximately fiber-free sample; and
providing the approximately fiber-free sample as the at least a first portion; determining a value indicative of a characteristic of the colloidal mixture by the steps of:
irradiating the at least a first portion of the colloidal mixture with light in an ultraviolet-visible region at a first temperature and obtaining a first measurement of a first wavelength within the ultraviolet-visible region, said first measurement for obtaining a measure of one of an absorption, emission and scattering of the first wavelength when said colloidal mixture is irradiated with the light;
waiting for the temperature of the colloidal mixture to change;
irradiating the at least a first portion of the colloidal mixture with light in an ultraviolet-visible region at a second different temperature and obtaining a second measurement of the first wavelength within the ultraviolet-visible region, said second measurement for obtaining a measure of one of an absorption, emission and scattering of the first wavelength when said colloidal mixture is irradiated with the light; and
determining the value indicative of the characteristic of the colloidal mixture from a relationship including the first measurement and the second measurement; determining, in dependence upon the determined value, an adjustment to the process parameter of the process involving the colloidal mixture; providing to an automated controller of the process involving the colloidal mixture a feedback signal in dependence upon the determined adjustment; and adjusting automatically the process parameter of the process in dependence upon the provided feedback signal.

13. A method for controlling a process parameter of a process involving a colloidal mixture according to claim 12, wherein the characteristic of the colloidal mixture is one of colloid tackiness and colloid propensity to deposit.

14. A method for controlling a process parameter of a process involving a colloidal mixture according to claim 12, wherein the colloidal mixture includes a plurality of colloidal particles and wherein the characteristic of the colloidal mixture is a determinant of a size distribution of the colloidal particles.

15. A method for controlling a process parameter of a process involving a colloidal mixture according to claim 13, wherein the in-line centrifuge unit operates in a batch mode.

16. A method for controlling a process parameter of a process involving a colloidal mixture according to claim 13, wherein the process parameter is a rate of addition of a chemical additive for affecting at least a characteristic of the colloidal mixture.

17. A method for controlling a process parameter of a process involving a colloidal mixture according to claim 16, wherein the chemical additive is one of a dispersant, a coagulant and an adsorber.

18. A method for controlling a characteristic of a colloidal mixture comprising the steps of:

providing a colloidal mixture for analysis by thermal difference spectroscopy; determining a value indicative of the characteristic of the colloidal mixture by the steps of:
irradiating at least a first portion of the colloidal mixture with light in an ultraviolet-visible region at a first temperature and obtaining at least a first measurement of a first and a second wavelength within the ultraviolet-visible region, said first measurement for obtaining one of an absorption, emission and scattering of the first wavelength when said colloidal mixture is irradiated with the light,
waiting for the temperature of the colloidal mixture to change,
irradiating at least a second portion of the colloidal mixture with light in an ultraviolet-visible region at a second different temperature and obtaining at least a second measurement of the first and the second wavelength within the ultraviolet-visible region, said second measurement for obtaining one of an absorption, emission and scattering of the second wavelength when said colloidal mixture is irradiated with the light, and
determining the value indicative of the characteristic of the colloidal mixture from a relationship including a ratio of the at least first and second measurement;
determining, in dependence upon the determined value, an adjustment to at least a variable of a control process for affecting at least a characteristic of the colloidal mixture;
providing a feedback signal in dependence upon the determined adjustment to an automated controller of the control process; and
adjusting automatically the variable of the control process in dependence upon the provided feedback signal.

19. A method for controlling a characteristic of a colloidal mixture according to claim 18, wherein the first portion and the second portion is substantially a same portion.

20. A method for controlling a characteristic of a colloidal mixture according to claim 19, wherein the characteristic of the colloidal mixture is one of colloid tackiness and colloid propensity to deposit.

21. A method for controlling a characteristic of a colloidal mixture according to claim 19, wherein the colloidal mixture includes a plurality of colloidal particles and wherein the characteristic of the colloidal mixture is a determinant of a size distribution of the colloidal particles.

22. A method for controlling a characteristic of a colloidal mixture according to claim 20, wherein the substantially a same portion is an approximately fiber-free portion of the colloidal mixture.

23. A method for controlling a characteristic of a colloidal mixture according to claim 22, wherein the approximately fiber-free portion of the colloidal mixture is provided using an in-line centrifuge unit.

24. A method for controlling a characteristic of a colloidal mixture according to claim 23, wherein the in-line centrifuge unit operates in a batch mode.

25. A method for controlling a characteristic of a colloidal mixture according to claim 23, wherein the variable of the control process is a rate of addition of a chemical additive for affecting at least a characteristic of the colloidal mixture.

26. A method for controlling a characteristic of a colloidal mixture according to claim 25, wherein the chemical additive is one of a dispersant, a coagulant and an adsorber.

27. A method for controlling a characteristic of a colloidal mixture according to claim 26, wherein the colloidal mixture includes a temperature sensitive component and a temperature insensitive component.

28. A method for controlling a characteristic of a colloidal mixture according to claim 20, wherein a difference between the first temperature and the second different temperature is at least 30° C.

29. An on-line optical sensor apparatus for controlling a process parameter of a process involving a colloidal mixture comprising:
  an in-line centrifuge unit for separating fiber from the colloidal mixture to obtain an approximately fiber-free liquid sample;
  a detector for obtaining a first measurement and a second measurement of light in an ultraviolet-visible region, said first measurement for obtaining a measure of one of an absorption, emission and scattering of at least a first wavelength of the light at a first temperature when the approximately fiber-free liquid sample of the colloidal mixture is irradiated with the light, and said second measurement for obtaining a measure of one of an absorption, emission and scattering of the first wavelength of the light at a second different temperature when the approximately fiber-free liquid sample of the colloidal mixture is irradiated with the light; and
  a suitably programmed processor in electrical communication with an automated process controller for providing thereto a signal indicative of an adjustment to the process parameter, wherein said adjustment is determined in dependence upon a characteristic of the colloidal mixture, and wherein said characteristic of the colloidal mixture is determined from a relationship including the first and second measurement.

30. An on-line optical sensor apparatus for controlling a process parameter of a process involving a colloidal mixture according to claim 29, wherein the suitably programmed processor and the process controller are in electrical communication via a feedback control circuit.

31. An on-line optical sensor apparatus for controlling a process parameter of a process involving a colloidal mixture according to claim 30, wherein the process controller is for controlling a rate of addition of a chemical additive for affecting at least a characteristic of the colloidal mixture.

32. An on-line optical sensor apparatus for controlling a process parameter of a process involving a colloidal mixture according to claim 30, wherein the in-line centrifuge comprises:
  a main centrifuge chamber being generally symmetrical about a central axis of rotation and having an opening in a first end thereof, the opening being approximately overlapping with the axis of rotation and, the opening for allowing an overflow of liquid within the centrifuge to pass therethrough;
  a sample introducer for introducing at least a batch sample of the colloid mixture from the process involving a colloidal mixture to the main centrifuge chamber; and
  a retaining portion in the first end of the main centrifuge chamber for retaining a first portion of the at least a batch sample of the colloid mixture and for providing a second portion of the at least a batch sample of the colloid mixture for analysis, wherein the second portion is the approximately fiber-free liquid sample of the colloidal mixture, and wherein the first portion is a fiber-enriched liquid sample of the colloidal mixture.

33. An on-line optical sensor apparatus for controlling a process parameter of a process involving a colloidal mixture according to claim 32, wherein the in-line centrifuge unit is in electrical communication with the suitably programmed processor, such that that operation of the in-line centrifuge unit is controlled by the processor.

34. An on-line optical sensor apparatus for controlling a process parameter of a process involving a colloidal mixture according to claim 33, comprising a sample holder in fluid communication with the in-line centrifuge unit for receiving the approximately fiber-free liquid sample of the colloidal mixture therefrom, the sample holder and the detector disposed within a same optical path such that, in use, ultraviolet light propagating along the same optical path passes through a first portion of the approximately fiber-free liquid sample of the colloidal mixture and is detected by the detector.

35. An on-line optical sensor apparatus for controlling a process parameter of a process involving a colloidal mixture according to claim 34, wherein the sample holder is a flow-through cell.

36. An on-line optical sensor apparatus for controlling a process parameter of a process involving a colloidal mixture according to claim 35, wherein the sample holder comprises a stirrer for, in use, agitating the approximately fiber-free liquid sample of the colloidal mixture contained therein.

37. An on-line optical sensor apparatus for controlling a process parameter of a process involving a colloidal mixture according to claim 36, wherein the sample holder is in thermal communication with a temperature control unit.

38. An on-line optical sensor apparatus for controlling a process parameter of a proess involving a colloidal mixture according to claim 37, wherein the temperature control unit includes a Peltier Effect thermoelectric heat pump.

* * * * *